(12) United States Patent
Finer et al.

(10) Patent No.: US 8,395,021 B2
(45) Date of Patent: Mar. 12, 2013

(54) HIGHLY ACTIVE SOYBEAN PROMOTER FROM THE SUBI-3 POLYUBIQUITIN GENE AND USES THEREOF

(75) Inventors: John J. Finer, Wooster, OH (US); Robert A. Bouchard, Wooster, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 402 days.

(21) Appl. No.: 12/598,975

(22) PCT Filed: May 8, 2008

(86) PCT No.: PCT/US2008/005972
§ 371 (c)(1),
(2), (4) Date: Dec. 31, 2009

(87) PCT Pub. No.: WO2008/140766
PCT Pub. Date: Nov. 20, 2008

(65) Prior Publication Data
US 2010/0186119 A1    Jul. 22, 2010

Related U.S. Application Data

(60) Provisional application No. 60/928,212, filed on May 8, 2007.

(51) Int. Cl.
*C12N 15/82*    (2006.01)

(52) U.S. Cl. ........ 800/278; 800/285; 800/286; 800/288; 800/289

(58) Field of Classification Search .................. None
See application file for complete search history.

(56) References Cited

U.S. PATENT DOCUMENTS

| 7,129,089 B2 | 10/2006 | Kinney et al. | |
| 7,393,948 B1 * | 7/2008 | Sekar et al. | 536/24.1 |
| 2007/0067865 A1 * | 3/2007 | Kovalic et al. | 800/278 |
| 2008/0250529 A1 | 10/2008 | Sekar et al. | |

OTHER PUBLICATIONS

PCT/US2008/005972 International Search Report and the Written Opinion dated Oct. 9, 2008.
PCT/US2008/005972 International Preliminary Report on Patentability dated Nov. 19, 2009.

* cited by examiner

*Primary Examiner* — Cathy Kingdon Worley
(74) *Attorney, Agent, or Firm* — MacMillan, Sobanski & Todd, LLC

(57) ABSTRACT

Soybean ubiquitin promoters is from the soybean SUBI-3 polyubiquitin gene and processes for expressing nucleic acids of interest in transgenic plants under the control of the soybean ubiquitin promoter pare described. Higher expression levels of the nucleic acids are achieved when the promoter is included.

10 Claims, 29 Drawing Sheets

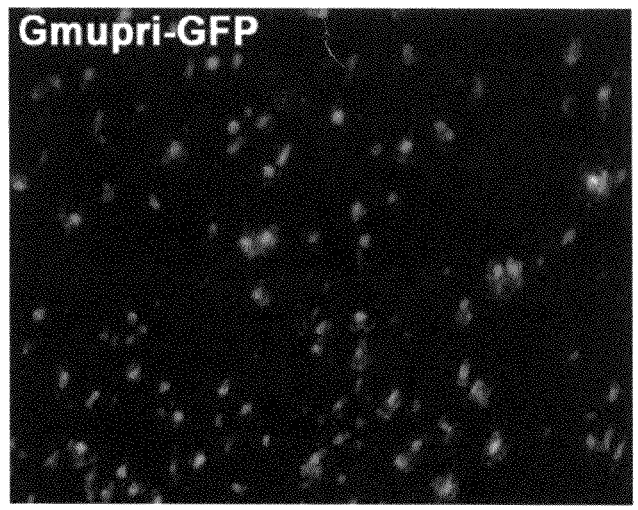
FIGURE 2 - Continued
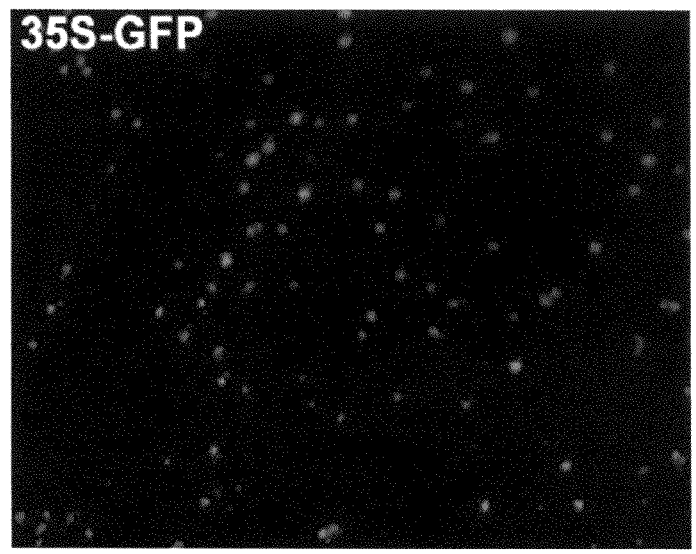
FIGURE 2 continued
|  | Total Expression | Foci | Mean Gray Value Pixel |
|---|---|---|---|
| Gmubi-GFP | 1942488 | 143 | 181 |
| Gmupri-GFP | 797926 | 93 | 120 |
| 35S-GFP | 340792 | 102 | 94 |
Figure 2 - continued GGGCCCAATATAACAACGACGTCGTAACAGATAAAGCGAAGCTTGAAGGTGCATGTGACTCCGTCAAGATTACG
AAACCGCCAACTACCACGCAAATTGCAATTCTCAATTTCCTAGAAGGACTCTCCGAAAATGCATCCAATCCAA
ATATTACCCGTGTCATAGCCACCAAGTGACACCTATACATGAACACGCGTCACAATATGACTGGAGAAGGGTTCC
ACACCTTATGCTATAAACGCCCCACAGCCCTCCTCCTTCCTTCGCAGTTCAATTCCAATATATTCCATTCTCT
CTTGTATGTTCTTGATCAATACCATGTTGATTTGATTGTGTTTTGTTTGGTTTCATCGATCTTCAATTTTCAT
AATCAGATTCAGCTTTTATTATCTTTACAACAACGTCCTTAATTTGATGATTCTTTAATCGTAGATTGCTCTA
ATTAGAGCTTTTTCATGTCAGATCCCTTTACAACAAGCCTTAATTGTTGATTCATTAATCGTAGATTAGGGCTT
TTTTCATTGATTACTTCAGATCCGTTAAACGTAACCATAGATCAGGGCTTTTCATGAATTACTTCAGATCCGT
TAAACAACAGCCTATTTTTATACTTCGTGGTTTTTCAAGAAATTGTTCAGATCGTTGACAAAAACCCCTTA
TTCGTTGATTCTATATCGTTTTCGAGAGATATTGCTCAGATCTGTTAGCAACTGCCTTGTTGTTGATTCTAT
TCCCCTGGATTAGGGTTTTTTTTCACCAGATTGCTTCAGATCCGTACTTAAGATTACGTAATGGATTTTGATTC
TGATTATCTGTGATTGTTGACTCGACAG

FIGURE 5 B – Gmubi Promoter [SEQ ID NO: 1]

TACATAAGTCTATCTAAAATGGAAAGATTGTTACCTAAFCTCAAATCATATTTTTCCCATCATAAAAAAAAAATC
TCAAATCATGTGATCTTGTCGATCATCATTTAATACATTATTAATTCTTCTTTTTAATTGAAAAATGTGATTAT
ATGTATGTGGAGATTAGTTCAGACCATGATCCTTGAATATGTAGTAAGTTTTTGTAATGTTGAGTTTGAGTTC
TTTGACACTAGGTCCATGTTTCCCAAAATTAAGTGTAAAAAATAAATAAAGAATTAAAAGTTGTGAAAAAATT
GTCCTCGTTTATTTTATTATTCAGAATTAATCTTTATTGACACTAAAATTATTTACAGAAAGTTAATACAGCA
CTAAAAGTTATTTTATTTTTTTGAGAAACAAAAACTGAAATCTAAAAAAAAATAAGAAACCGGAAATCTAATTA
ACAAAAATATATACGGGCTAACATGGTTATGGGCTTAGGCTGCCTCATTACCCATTACATGCTCTGTTCCTAAA
AAAAAAAAGAAGTTTGGGCCTTTATCCTCCAGTAAGTTTTTTAATTGGGCTCAAGAACTTTAGGATTTAGGTGA
GGATCAATGAAAGTTTATATATTAGGCTTGATTTTTTTTCAATTTACGTAAAAATGAAAGAAAAAGTCACACT
CTATAAACTTTATTTTTTTCAATATTAATACATTGTTATTGTGGATATATCATTAGCGGAAAAGTAATTCTAAT
ACCAGATTTAATTGACTTTGACTAAATTTTTTTAGCGGAATAAAAGTTTTGNTACTTTGNCGCGTGATTTTTAAT
SNAACTTTGGGGATAATTTCCCCTCCAATTCAGCCCAAAAAAAAAAAAACTGANGBCATATNTATTAGTAGGC
AACTTGTTCGTAAATGGTGTGGCTTATCCGAATGGAAATGGATTCGTTTCTTTAACATCATTATTGTTTTTG
TCAATGAGCTATCTTTTAGTCTTATGTTATTGGTGAATCTGTCCTTAAGTTGCATCATTTAACACATCTCCTCA
TTAGAGAAAAAATTCTTCCCTAAACGATTGGTAGTAAAAACATCTAATAAGAAATAAGAAGAAAAATTAGGA
AAAAGGAAAGTTCATTAAAAAAAATATTTGAATTATTTTTTAAAAAATATCTAAATATTTTTTAAATGAATAA
TTTTATATAAACTGTAACTAAATGTATACAAGTAATGTATGTTAAAAAAATACTTGAAAAATCTACTGAAAATA
TATCTTACAAGGTGAAATTAAATAAGAAAGAATTTAGTGGAATAATTATGATTTATTTAAAAAATAATTATTA
AAGATTTTTTTGCTCCATAATAAGAAAACTTTTCAATTATTCTTTTCTGGTCCATAATAAAAAAAAATCTAGCAT
GACAGCTTTTCCATAGATTTTTAATAATGTAAAAGCAGCCGACTTCAGGCAATGGATAGTGGGGCCCGTATCAA
CTTCGGACGCTCCACTTGCAACGGGGTGGGCCCAATATAACAACGACGTCGTAACAGATAAAGCGAAGCTTGAA
GGTGCATGTGACTCCGTCAAGATTACGAAACCGCCAACTACCACGCAAATTGCAATTCTCAATTTCCTAGAAGG

FIGURE 6B – 1500Gmubi [SEQ ID NO: 2]

ACTCTCCGAAAATGCATCCAATACCAAATATTACCCGTGTCATAGGCACCAAGTGACACCATACATGAACACGC
GTCACAATATGACTGGAGAAGGGTTCCACACCTTATGCTATAAAACGCCCCACACCCCTCCTCCTTCCTTCGCA
GTTCAATTCCAATATATTCCATTCTCTCTGTGTATTTCCCTACCTCTCCCTTCAAGGTTAGTCGATTTCTTCTG
TTTTTCTTCTTCGTTCTTTCCATGAATTGTGTATGTGTCTTTGATCAATACGATGTTGATTTGATTGTGTTTGT
TTGGTTTCATCGATCTTCAATTTTCATAATCAGATTCAGCTTTTATTATCTTTACAACAACGTCCTTAATTTGA
TGATTCTTTAATCGTAGATTTGCTCTAATTAGAGCTTTTTCATGTCAGATCCCTTTACAACAAGCCTTAATTGT
TGATTCATTAATCGTAGATTAGGGCTTTTTTCATTGATTACTTCAGATCCGTTAAACGTAACCATAGATCAGGG
CTTTTCATGAATTACTTCAGATCCGTTAAACAACAGCCTTATTTTTATACTTCTGTGGTTTTTCAAGAAATT
GTTCAGATCCGTTGACAAAAGCCTTATTCGTTGATTCTATATGTTTTTCGAGAGATATTGCTCAGATCTGTT
AGCAACTGCCTTGTTTGTTGATTCTATTGCCGTGGATTAGGGTTTTTTTTCACGAGATTGCTTCAGATCCGTAC
TTAAGATTACGTAATGGATTTTGATTCTGATTTATCTGTGATTGTTGACTCGACAG

FIGURE 6B CONT. – 1500 Gmubi [SEQ. ID NO: 2]

GGGCCCAATATAACAACGACGTCGTAACAGATAAAGCGAAGCTTGAAGGTGCATGTGACTCCGTCAAGATTACG
AAACCGCCAACTACCACGCAAATTGCAATTCTCAATTTCCTAGAAGGACTCTCCGAAAATGCATCCAATACCAA
ATATTACCCGTGTCATAGGCACCAAGTGACACCATACATGAACACGCGTCACAATATGACTGGAGAAGGGTTCC
ACACCTTATGCTATAAAACGCCCCACACCCCTCCTCCTTCCTTCGCAGTTCAATTCCAATATATTCCATTCTCT
CTGTGTATTTCCCTACCTCTCCCTTCAAG

FIGURE 7B – Gmupri (Gmubi pre-intronic) Promoter [SEQ ID NO: 3]

CTATAAAACGCCCCTACACCCCTCCTCCTTCCTTCGCAGTTCAATTCCAATATATTCCATTCTATCTGTGTATT
TCCCTACCGCACCCTTCAAG

FIGURE 8B CONT. – Gmucor (Minimal) Promoter [SEQ ID NO: 5]

CCATGGACTTTAACAGCAACACAATTTACAATCTAAAATGTATTACTTTTTTTTTCAAAAAAGATATACAAAAT
AAGGTACCAAGAATAAAAGGAGTATTTAGAAACAGCGGCACCAATTTAATAAATTATTTATATAAAACGACACT
TATTTAATTTATCAATGATAAAAGTAATATTGATTTATTCTCTGATTAACTGTTCAATTAATGGTGTTATTATC
ATAATCTGTCGCAAAAGTTATTTTTATCAACAACAATAATTGATACAAGTAGTATAAAATTAAGCCTCTTAGTT
AATATAGACTACTTGATACTAAAACCATGTTACACCAAAAAGTAATTTTTATGTCACTTGTCTATATAATAATT
ACGACTAAATTAATAATTTTTAAAAATATTACTGAATCCATTAACCGAACTTTNATAATGAAAGTATTTTTATG
CTTNAAAATCACAACCTTGAATAAACTAAAAATGATACCACGGAATTGGAACAAGAGACGTGCCACACAAAAGA
AAAAAATATGTCGAATAATTGAAACGGTGACAAGAAAAGTGGAATAATAATACAAAGATGGCAGATGGGGTTAT
TGTTATTGGAGGAGATGAGTGAAATAATGAGTGAGGGGGGTGTAACTGGAAAGCAAGAAAAAGCGCAAGAGTGC

FIGURE 9B – Gmactin Promoter [SEQ ID NO: 7]

Gmucor Promoter

Gmactin Promoter

CAGCTATTTCCAACAACAAACGTGGCCCGTGGGATGCGATATTCGTAACGAACGGCGAGGATGGAAGGACGTGC
AATTTGCGCTTCATTTGAGGCGAATTTCATTTGGCCAGACCTTCCTTTTTTAAACCACAGGGCGGGTACCTCAG
CCACACACACACAAATTCACACAAACATAAAAAAAAAAAAAAAAAAACACACGCACTCTCATACACACGTTG
TCGCGCACACATTCCTTCATTCCGCAGGTATCGCCACGTTCTCTCTTCCCTCTTTCATCCCCCCGATAAGAACA
AGCACCCACCGTTTAACGCTAATTTTTGAGTGTTTTTGTTTTTTGCAGCAACAAACAAACATCTTTTACCTTAA
ACAACCATGG

FIGURE 9 - Gmactin Promoter [SEQ ID NO: 7]

ATCTACAAGTATAGGTTATTTGTCATGCCTACTCACCAAACACCTCTATTCCAGAATGGTAATTCTGAACTATT
CCAAAATATGACTTTTTCTTAATCCAGAATATGTATTTTCGAACAGGTTTTCGAATTACTTATCCTATTAAGGA
ATAACTATTCTAGAAAATAAGAATTATGTTGGAGGGACCTATGGGGTGGTGACGTGTGACTGTGGACAACGTGG
TGGTGGTGTTGCACACGGATCTGGAGGAAGGTGGGGGTGACAGAGTGTTGCTGGTGATGATGGCAAGGGTTTCC
TTGGGAGAGGGAGGAATGCCTAGTGAGGGGTTACTTAGGTCTGTTGGATCTTCTGGAGATGCAGGAAGAAAAA
AGGAGGTACAGGAACTAATTCCCTAGAGTCCTGGCAAAATTAGCTAAATTATTATTATGAGCCTCAAATTGAAA
TTTGGGCTAGCCCATCTAATAAAGTCCAGGAGTTTGAAGATGGAAAAGAAAGGGTGTTATAAAAACTACTCTCA
TCACTACTCATTAGGGTTTCTGGATGCTGCTAGTTTCTGTCTGAAAGCTATTCTCCACCGTAGCCGCAAGCTTC
GCCGTTTGAAACAGTGCCTCAACC

FIGURE 10B - GmS11 Promoter [SEQ ID NO: 10]

AAATAAATGGAAATCCACTCTAAAAAAAATAATGAAGAAATGAAAAACATAAAATATTGAATTAAAAAAATTA
AATAAAGGCACGTTGAAAACGAATATAAAAAAAATAAAAAAAAATGGCAGGTTGAGAAATCAGGGCATGGAAAA
TCGATTTCTCAATATTAAAAGCAAAATAATCTTGATTGCATATTAAAAATTCGGTTTGGAGATGACTGATTTA
TCTTAGGAATGGTATGATTTGTATTACTTTGGTAAATATTTTGACATACATTATTTGTGTAATTTTTTTATGT
TTGAGTTAAAAAGACTCCCCATATAGTTAGGTTCCTAGTCAATCATTTGTGGTTGGTTTTGGTAAATACTACTG
ATGAGTTATTTATTTTTAAAAAATAAAGACGAGGATTTGAAATTTAGAATAAGATTAGATCTACAAAATTTAT
TTTTATAAAGACAGAGTTAAAGATTTATTACTGATAAAAAAAAAAAGAAGAGGATTTGAAATTTAGAACAAGA
TTAGATTGGTGTAACGTGAACCACGCGATGTTGATTACTATTTTACATTAGAATGTTAATTTTTAGGCGAAGCC
GGCTTAACGTAACAATTACGAGTGACGAGTCGGTCAGATAGAAGGATCTAGAAAAGCAAGTCGTCGCTATATAA
CTAAGGGATCCGTCACGGAAGGATCTAGAAACCCTAGTAGTGAACCCTCTCTATAAAACCTCTTCCTTCTTTCA
TTCGGTGCCTATTCCCATTTTCTTCCTCTAAACCCTAAACAACTCTTTCTCTTCTTCCTTCGCTCGTCGTTCTC
CCTCGCGTAGATCGA

FIGURE 11B - GmHSP90L-830 Promoter [SEQ ID NO: 15]

CAGCTATTTCCAACAACAAACGTGGCCCGTGGGATGCGATATTCGTAACGAACGGCGAGGATGGAAGGACGTGC
AATTGCGCTTCATTTGAGGCGAATTTCATTTGGCCAGACCTTCCTTTTTTAAACCACAGGGCGGGTACCTCAG
CCACACACACACAAATTCACACAAACATAAAAAAAAAAAAAAAAAAAACACACACGCACTCTCATACACAGTTG
TCGCGCACACATTCCTTCATTCCGCAGGTATCGCCACGTTCTCTCTTCCCTCTTTCATCCCCCCGATAAGAACA
AGCACCCACCGTTAACGCTAATTTTTGAGTGTTTTTGTTTTTGCAGCAACAAACAAACATCTTTTACCTTAA
ACAACCATGG

FIGURE 9B CONT. – Gmactin Promoter [SEQ ID NO: 7]

ATCTACAAGTATAGGTTATTTGTCATGCCTACTCACCAAACACCTCTATTCCAGAATGGTAATTCTGAACTATT
CCAAAATATGACTTTTTCTTAATCCAGAATATGTATTTTCGAACAGGTTTTCGAATTACTTATCCTATTAAGGA
ATAACTATTCTAGAAAATAAGAATTATGTTGGAGGGACCTATGGGGTGGTGACGTGTGACTGTGGACAACGTGG
TGGTGGTGTTGCACACGGATCTGGAGGAAGCTGGGGGTGACAGAGTGTTGCTGGTGATGATGGCAAGGGTTTCC
TTGGGAGAGGGAGGAATGCCTAGTGAGGGGTTACTTAGGTCTGTTGGATCTTCTGGAGATGCAGGAAGAAAAAA
AGGAGGTACAGGAACTAATTCCCTAGAGTCCTGGCAAAATTAGCTAAATTATTATTATGAGCCTCAAATTGAAA
TTTGGGCTAGCCCATCTAATAAAGTCCAGGAGTTTGAACATGCAAAAGAAAGGGTGTTATAAAAACTACTCTCA
TCACTACTCATTAGGGTTTCTGGATGCTGCTAGTTTCTGTCTGAAAGCTATTCTCCACCGTAGCCGCAAGCTTC
GCCGTTTGAAACAGTGCCTCAACC

FIGURE 10B - GmS11 Promoter [SEQ ID NO: 10]

AAATAAATGGAAATCCACTCTAAAAAAAATAATGAAGAAATGAAAAACATAAAATATTGAATTAAAAAAATTA
AATAAAGGCACGTTGAAAACGAATATAAAAAAAATAAAAAAAAATGGCAGGTTGAGAAATCAGGGCATGGAAAA
TCGATTTCTCAATATTAAAAGCAAAAATAATCTTGATTGCATATAAAAATTCGGTTTGCAGATGACTGATTTA
TCTTAGGAATGGTATGATTTGTATTACTTTGGTAAATATTTTGACATACATTATTTGTGTAATTTTTTTATGT
TTGAGTTAAAAAGACTCCCCATATAGTTAGGTTCCTAGTCAATCATTTGTGGTTGGTTTTGGTAAATACTACTG
ATGAGTTATTTATTTTTAAAAAATAAAGACGAGGATTTGAAATTTAGAATAAGATTAGATCTACAAAATTTAT
TTTTATAAAGACAGAGTTAAAGATTTATTACTGATAAAAAAAAAAAGAAGAGGATTTGAAATTTAGAACAAGA
TTAGATTGGTGTAACGTGAACCACGCGATGTTGATTACTATTTTACATTAGAATGTTAATTTTTAGGCGAAGCC
GGCTTAACGTAACAATTACGAGTGACGAGTCGGTCAGATAGAAGGATCTAGAAAAGCAAGTCGTCGCTATATAA
CTAAGGGATCCGTCACGGAAGGATCTAGAAACCCTAGTAGTGAACCCTCTCTATAAAACCTCTTCCTTCTTTCA
TTCGGTGCCTATTCCCATTTTCTTCCTCTAAACCCTAAACAACTGTTCTCTTCTTCCTTCGCTCGTCGTTCTC
CCTCGCGTAGATCGA

FIGURE 11B - GmHSP90L-830 Promoter [SEQ ID NO: 15]

```
GTTTGGAGATGACTGATTTATCTTAGGAATGGTATGATTTGTATTACTTTGGTAAATATTTTGACATACATTAT
TTGTGTAATTTTTTTTATGTTTGAGTTAAAAAGACTCCCCATATAGTTAGGTTCCTAGTCAATCATTTGTGGTT
GGTTTTGGTAAATACTACTGATGAGTTATTTATTTTTAAAAAATAAAGACGAGGATTTGAAATTTAGAATAAG
ATTAGATCTACAAAATTTATTTTTATAAAGACAGAGTTAAAGATTTATTACTGATAAAAAAAAAAAAGAAGAGG
ATTTGAAATTTAGAACAAGATTAGATTGGTGTAACGTGAACCACGCGATGTTGATTACTATTTTACATTAGAAT
GTTAATTTTTAGGCGAAGCCGGCTTAACGTAACAATTACGAGTGACGAGTCGGTCAGATAGAAGGATCTAGAAA
AGCAAGTCGTCGCTATATAACTAAGGGATCCGTCACGGAAGGATCTAGAAACCCTAGTAGTGAACCCTCTCTAT
AAAACCTCTTCCTTCTTTCATTCGGTGCCTATTCCCATTTTCTTCCTCTAAACCCTAAACAACTCTTTCTCTTC
TTCCTTCGCTCGTCGTTCTCCCTCGCGTAGATCGA
```

FIGURE 11C - GmHSP90L-628 Promoter [SEQ ID NO: 20]

```
AAAAAATAAAGACGAGGATTTGAAATTTAGAATAAGATTAGATCTACAAAATTTATTTTTATAAAGACAGAGTT
AAAGATTTATTACTGATAAAAAAAAAAAAGAAGAGGATTTGAAATTTAGAACAAGATTAGATTGGTGTAACGTG
AACCACGCGATGTTGATTACTATTTTACATTAGAATGTTAATTTTTAGGCGAAGCCGGCTTAACGTAACAATTA
CGAGTGACGAGTCGGTCAGATAGAAGGATCTAGAAAAGCAAGTCGTCGCTATATAACTAAGGGATCCGTCACGG
AAGGATCTAGAAACCCTAGTAGTGAACCCTCTCTATAAAACCTCTTCCTTCTTTCATTCGGTGCCTATTCCCAT
TTTCTTCCTCTAAACCCTAAACAACTCTTTCTCTTCTTCCTTCGCTCGTCGTTCTCCCTCGCGTAGATCGA
```

Figure 11D - GmHSP90L-443 Promoter [SEQ ID NO: 16]

```
CGTAACAATTACGAGTGACGAGTCGGTCAGATAGAAGGATCTAGAAAAGCAAGTCGTCGCTATATAACTAAGGG
ATCCGTCACGGAAGGATCTAGAAACCCTAGTAGTGAACCCTCTCTATAAAACCTCTTCCTTCTTTCATTCGGTG
CCTATTCCCATTTTCTTCCTCTAAACCCTAAACAACTCTTTCTCTTCTTCCTTCGCTCGTCGTTCTCCCTCGCG
TAGATCGA
```

FIGURE 11E - GmHSP90L-231 Promoter [SEQ ID NO: 21]

```
CGTCGCTATATAACTAAGGGATCCGTCACGGAAGGATCTAGAAACCCTAGTAGTGAACCCTCTCTATAAAACCT
CTTCCTTCTTTCATTCGGTGCCTATTCCCATTTTCTTCCTCTAAACCCTAAACAACTCTTTCTCTTCTTCCTTC
GCTCGTCGTTCTCCCTCGCGTAGATCGA
```

Figure 11F - GmHSP90L-177 Promoter [SEQ ID NO: 22]

| Soybean Promoter GFP Stable Events | | | |
|---|---|---|---|
| Promoter | No. of clones | Status of clones | Confirmation of transformation |
| Gmubi | 17 | seed from 14 clones | Southern+ and GFP+ |
| Gmupri | 54 | seed from 36 clones | Southern+ and GFP+ |
| GmActin | 39 | seed from 27 clones | PCR+, and GFP+ |
| HSP-830 | 29 | seed from 26 clones | PCR+, and GFP+ |
| HSP-443 | 31 | seed from 27 clones | PCR+, and GFP+ |
| GmS11 | 7 | seed from 6 clones | Southern+ and GFP+ |

FIGURE 17

| Soybean Promoter GFP Stable Events – Tissue-specific expression | |
|---|---|
| 35S | D20, roots, leaves |
| GmActin | D20, DevSE, roots |
| Gmubi | D20, roots, leaves |
| Gmupri (pre-intronic) | D20, roots |
| GmS11 | E tissue, root initials |
| HSP90-830 | Newly forming embryos |
| HSP90-443 | D20 tissue |

FIGURE 18

Petiole

Leaf

Shoot tip

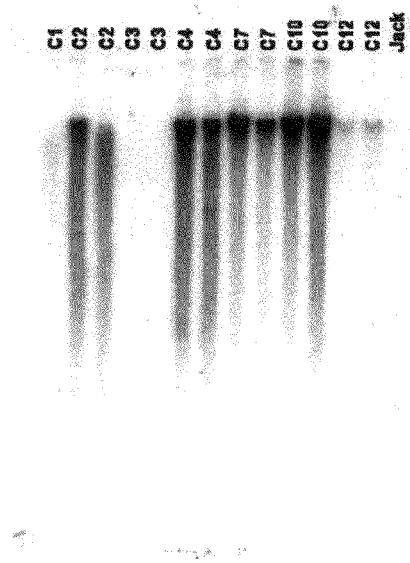
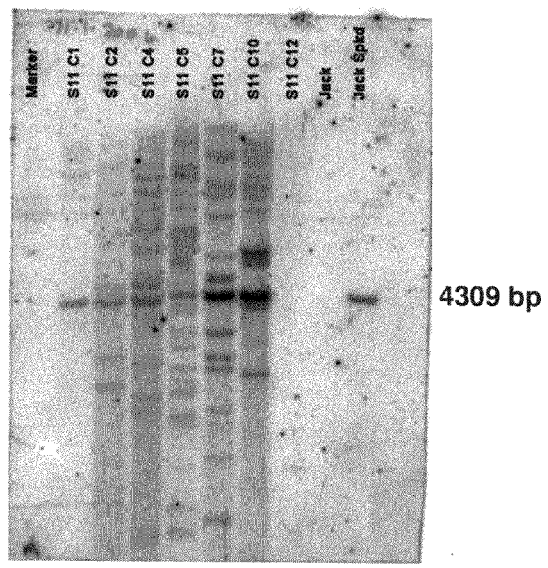
FIGURE 26A
FIGURE 26B

SEQUENCE LISTING

```
<160> NUMBER OF SEQ ID NOS: 22

<210> SEQ ID NO 1
<211> LENGTH: 917
<212> TYPE: DNA
<213> ORGANISM: Glycine max

<400> SEQUENCE: 1
gggcccaata taacaacgac gtcgtaacag ataaagcgaa gcttgaaggt gcatgtgact      60
ccgtcaagat tacgaaaccg ccaactacca cgcaaattgc aattctcaat ttcctagaag     120
gactctccga aaatgcatcc aataccaaat attacccgtg tcataggcac caagtgacac     180
catacatgaa cacgcgtcac aatatgactg gagaagggt ccacaccta tgctataaaa       240 cgccccacac ccctcctcct tccttcgcag ttcaattcca atatattcca ttctctctgt     300
gtatttccct acctctccct tcaaggttag tcgatttctt ctgttttct tcttcgttct      360 ttccatgaat tgtgtatgtt ctttgatcaa tacgatgttg atttgattgt gttttgtttg     420
gtttcatcga tcttcaattt tcataatcag attcagcttt tattatcttt acaacaacgt     480
ccttaatttg atgattcttt aatcgtagat ttgctctaat tagagctttt tcatgtcaga     540 tcccttaca acaagcctta attgttgatt cattaatcgt agattagggc ttttttcatt     600
gattacttca gatccgttaa acgtaaccat agatcagggc tttttcatga attacttcag     660
atccgttaaa caacagcctt attttttata cttctgtggt tttcaagaa attgttcaga     720 tccgttgaca aaaagcctta ttcgttgatt ctatatcgtt tttcgagaga tattgctcag     780
```

```
atctgttagc aactgccttg tttgttgatt ctattgccgt ggattagggt ttttttttcac      840 gagattgctt cagatccgta cttaagatta cgtaatggat tttgattctg atttatctgt      900
gattgttgac tcgacag                                                     917

<210> SEQ ID NO 2
<211> LENGTH: 2424
<212> TYPE: DNA
<213> ORGANISM: Glycine max
<220> FEATURE:
<221> NAME/KEY: modified_base
<222> LOCATION: (791)
<223> OTHER INFORMATION: a, c, g, t, unknown or other
<220> FEATURE:
<221> NAME/KEY: modified_base
<222> LOCATION: (799)
<223> OTHER INFORMATION: a, c, g, t, unknown or other
<220> FEATURE:
<221> NAME/KEY: modified_base
<222> LOCATION: (815)..(816)
<223> OTHER INFORMATION: a, c, g, t, unknown or other
<220> FEATURE:
<221> NAME/KEY: modified_base
<222> LOCATION: (868)..(870)
<223> OTHER INFORMATION: a, c, g, t, unknown or other
<220> FEATURE:
<221> NAME/KEY: modified_base
<222> LOCATION: (876)
<223> OTHER INFORMATION: a, c, g, t, unknown or other
<220> FEATURE:
<221> NAME/KEY: modified_base
<222> LOCATION: (928)
<223> OTHER INFORMATION: a, c, g, t, unknown or other

<400> SEQUENCE: 2
tacataagtc tatctaaaat ggaaagattg ttacctaatc tcaaatcata ttttttcccat      60 cataaaaaaa aatctcaaat catgtgatct tgtcgatcat catttaatac attattaatt     120
cttcttttta attgaaaaat gtgattatat gttatgtgga gattagttca gaccatgatc     180
cttgaatatg tagtaagttt ttgtaatgtt gagtttgagt tctttgacac taggtccatg     240
tttcccaaaa ttaagtgtaa aaataaaata aagaattaaa agttgtgaaa aaaattgtcc     300
tcgtttattt ttattattca gaattaatct ttattgagac taaaattatt tacagaaagt     360
taatacagca ctaaaagtta ttttatttttt ttgagaaaca aaaactgaaa tctaaaaaaa     420
aataagaaac cggaaatcta attaacaaaa atatatacgg gctaacatgg ttatgggctt     480
aggctgcctc attacccatt acatgctctg ttcctaaaaa aaaaaagaag tttgggcctt     540
tatcctccag taagtttttt aattgggctc aagaactttta ggatttaggt gaggatcaat     600
gaaagtttat atattaggct tgattttttt ttcaatttac gtaaaaatga agaaaaagt     660 cacactctat aaactttatt tttttcaata ttaatacatt gttattgtgg atatatcatt     720
agcggaaaag taattctaat accagattta attgactttg actaattttt ttagcggaat     780
aaaagttttg ntactttgnc gcgtgatttt taatnnaact ttggggataa tttcccctcc     840
aattcagccc aaaaaaaaaa aaactgannn catatnttat tagtaggcaa cttgttcgta     900
aatggtgtgg cttatccgaa tggaaatngg attcgttttc tttaacatca ttattgtttt     960
tgtcaatgag ctatctttta gtcttatgtt attggtgaat ctgtccttaa gttgcatcat    1020
ttaacacatc tcctcattag agaaaaaaat tcttccctaa acgattggta gtaaaaacat    1080
ctaataagaa ataagaaaga aaattaggaa aaaggaaag ttcattaaaa aaaatatttt    1140
gaattatttt ttaaaaaata tctaaatatt ttttaaatga ataattttat ataaactgta    1200
actaaatgta tacaagtaat gtatgttaaa aaaatacttg aaaaatctac tgaaaatata    1260
```

```
tcttacaagg tgaaattaaa taagaaagaa tttagtggaa taattatgat tttatttaaa      1320
aaataattat taaagatttt tttgctccat aataagaaaa cttttcaatt attcttttct      1380
ggtccataat aaaaaaaatc tagcatgaca gcttttccat agattttta aatgtaaaa        1440 gcagccgact tcaggcaatg gatagtgggg cccgtatcaa cttcggacgc tccacttgca      1500
acggggtggg cccaatataa caacgacgtc gtaacagata aagcgaagct tgaaggtgca      1560
tgtgactccg tcaagattac gaaaccgcca actaccacgc aaattgcaat tctcaatttc      1620
ctagaaggac tctccgaaaa tgcatccaat accaaatatt acccgtgtca taggcaccaa      1680
gtgacaccat acatgaacac gcgtcacaat atgactggag aagggttcca cacttatgc      1740 tataaaacgc cccacacccc tcctccttcc ttcgcagttc aattccaata tattccattc      1800
tctctgtgta tttccctacc tctcccttca aggttagtcg atttcttctg tttttcttct     1860
tcgttctttc catgaattgt gtatgttctt tgatcaatac gatgttgatt tgattgtgtt     1920
ttgtttggtt tcatcgatct tcaattttca taatcagatt cagcttttat tatctttaca    1980
acaacgtcct taatttgatg attctttaat cgtagatttg ctctaattag agcttttca     2040 tgtcagatcc ctttacaaca agccttaatt gttgattcat taatcgtaga ttagggcttt     2100
tttcattgat tacttcagat ccgttaaacg taaccataga tcagggcttt ttcatgaatt    2160
acttcagatc cgttaaacaa cagccttatt ttttatactt ctgtggtttt tcaagaaatt    2220
gttcagatcc gttgacaaaa agccttattc gttgattcta tatcgttttt cgagagatat   2280
tgctcagatc tgttagcaac tgccttgttt gttgattcta ttgccgtgga ttagggtttt   2340
ttttcacgag attgcttcag atccgtactt aagattacgt aatggatttt gattctgatt   2400
tatctgtgat tgttgactcg acag                                            2424
```

<210> SEQ ID NO 3
<211> LENGTH: 325
<212> TYPE: DNA
<213> ORGANISM: Glycine max

<400> SEQUENCE: 3

```
gggcccaata taacaacgac gtcgtaacag ataaagcgaa gcttgaaggt gcatgtgact       60
ccgtcaagat tacgaaaccg ccaactacca cgcaaattgc aattctcaat ttcctagaag      120
gactctccga aaatgcatcc aataccaaat attacccgtg tcataggcac caagtgacac      180
catacatgaa cacgcgtcac aatatgactg gagaagggtt ccacacctta tgctataaaa      240
cgccccacac ccctcctcct tccttcgcag ttcaattcca atatattcca ttctctctgt      300
gtatttccct acctctccct tcaag                                            325
```

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
cggatccttg aagggtgcgg tagggaaat                                         29
```

<210> SEQ ID NO 5
<211> LENGTH: 94
<212> TYPE: DNA
<213> ORGANISM: Glycine max

-continued

```
<400> SEQUENCE: 5
ctataaaacg cccctacacc cctcctcctt ccttcgcagt tcaattccaa tatattccat      60
tctatctgtg tatttcccta ccgcacccct caag                                  94

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtcgactat aaaacgcccc tacaccc                                          27

<210> SEQ ID NO 7
<211> LENGTH: 1046
<212> TYPE: DNA
<213> ORGANISM: Glycine max
<220> FEATURE:
<221> NAME/KEY: modified_base
<222> LOCATION: (424)
<223> OTHER INFORMATION: a, c, g, t, unknown or other
<220> FEATURE:
<221> NAME/KEY: modified_base
<222> LOCATION: (448)
<223> OTHER INFORMATION: a, c, g, t, unknown or other

<400> SEQUENCE: 7
ccatggactt taacagcaac acaatttaca atctaaaatg tattactttt tttttcaaaa      60
aagatataca aaataaggta ccaagaataa aaggagtatt tagaaacagc ggcaccaatt     120
taataaatta tttatataaa acgacactta tttaatttat caatgataaa agtaatattg     180
atttattctc tgattaactg ttcaattaat ggtgttatta tcataatctg tcgcaaaagt     240
tatttttatc aacaacaata attgatacaa gtagtataaa attaagcctc ttagttaata     300
tagactactt gatactaaaa ccatgttaca ccaaaaagta attttttatgt cacttgtcta     360 tataataatt acgactaaat taataatttt taaaaatatt actgaatcca ttaaccgaac     420
tttnataatg aaagtatttt tatgcttnaa aatcacaacc ttgaataaac taaaaatgat     480
accacggaat tggaacaaga gacgtgccac acaaaagaaa aaaatatgtc gaataattga     540
aacggtgaca agaaaagtgg aataataata caaagatggc agatgggtt attgttattg     600 gaggagatga gtgaaataat gagtgagggg ggtgtaactg gaaagcaaga aaaagcgcaa     660
gagtgccagc tatttccaac aacaaacgtg gcccgtggga tgcgatattc gtaacgaacg     720
gcgaggatgg aaggacgtgc aatttgcgct tcatttgagg cgaatttcat ttggccagac     780
cttccttttt taaccacag ggcgggtacc tcagccacac acacacaaat tcacacaaac     840
ataaaaaaaa aaaaaaaaa acacacacgc actctcatac acacgttgtc gcgcacacat     900
tccttcattc cgcaggtatc gccacgttct ctcttccctc tttcatcccc ccgataagaa     960
caagcaccca ccgtttaacg ctaattttg agtgttttg tttttgcag caacaaacaa    1020 acatcttta ccttaaacaa ccatgg                                         1046

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 8
caaacgaggg gttgaatatc ctcggcatc                                          29

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccatggttg tttaaggtaa aagatgtttg tttgt                                   35

<210> SEQ ID NO 10
<211> LENGTH: 616
<212> TYPE: DNA
<213> ORGANISM: Glycine max

<400> SEQUENCE: 10
atctacaagt ataggttatt tgtcatgcct actcaccaaa cacctctatt ccagaatggt        60
aattctgaac tattccaaaa tatgactttt tcttaatcca gaatatgtat tttcgaacag       120
gttttcgaat tacttatcct attaaggaat aactattcta gaaaataaga attatgttgg       180
agggacctat ggggtggtga cgtgtgactg tggacaacgt ggtggtggtg ttgcacacgg       240
atctggagga aggtgggggt gacagagtgt tgctggtgat gatggcaagg gtttccttgg       300
gagagggagg aatgcctagt gaggggttac ttaggtctgt tggatcttct ggagatgcag       360
gaagaaaaaa aggaggtaca ggaactaatt ccctagagtc ctggcaaaat tagctaaatt       420
attattatga gcctcaaatt gaaatttggg ctagcccatc taataaagtc caggagtttg       480
aagatggaaa agaaagggtg ttataaaaac tactctcatc actactcatt agggtttctg       540
gatgctgcta gtttctgtct gaaagctatt ctccaccgta gccgcaagct tcgccgtttg       600
aaacagtgcc tcaacc                                                      616

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggttgcttca gaaaagcctt ctctgtttgt tc                                      32

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccatggttg aggcactgtt tcaaacg                                            27

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 13
tcagcctgga aagcaaacgt ctctgtctc                                              29

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccatggtcg atctacgcga gggagaac                                               28

<210> SEQ ID NO 15
<211> LENGTH: 829
<212> TYPE: DNA
<213> ORGANISM: Glycine max

<400> SEQUENCE: 15
aaataaatgg aaatccactc taaaaaaaat aatgaagaaa tgaaaaacat aaatattga              60 attaaaaaaa attaaataaa ggcacgttga aaacgaatat aaaaaaaata aaaaaaaatg           120
gcaggttgag aaatcagggc atggaaaatc gatttctcaa tattaaaagc aaaaataatc           180
ttgattgcat attaaaaatt cggtttggag atgactgatt tatcttagga atggtatgat           240
ttgtattact ttggtaaata ttttgacata cattatttgt gtaattttt ttatgtttga            300 gttaaaaaga ctcccccatat agttaggttc ctagtcaatc atttgtggtt ggttttggta          360
aatactactg atgagttatt tattttttaa aaaataaaga cgaggatttg aaatttagaa           420
taagattaga tctacaaaat ttatttttat aaagacagag ttaaagattt attactgata           480
aaaaaaaaaa agaagaggat tgaaattta gaacaagatt agattggtgt aacgtgaacc            540
acgcgatgtt gattactatt ttacattaga atgttaattt ttaggcgaag ccggcttaac           600
gtaacaatta cgagtgacga gtcggtcaga tagaaggatc tagaaaagca agtcgtcgct           660
atataactaa gggatccgtc acggaaggat ctagaaaccc tagtagtgaa ccctctctat           720
aaaacctctt ccttctttca ttcggtgcct attcccattt tcttcctcta aaccctaaac           780
aactctttct cttcttcctt cgctcgtcgt tctccctcgc gtagatcga                       829

<210> SEQ ID NO 16
<211> LENGTH: 441
<212> TYPE: DNA
<213> ORGANISM: Glycine max

<400> SEQUENCE: 16
aaaaaataaa gacgaggatt tgaaatttag aataagatta gatctacaaa atttattttt            60
ataaagacag agttaaagat ttattactga taaaaaaaaa aagaagagga tttgaaatt            120 tagaacaaga ttagattggt gtaacgtgaa ccacgcgatg ttgattacta ttttacatta          180
gaatgttaat ttttaggcga agccggctta acgtaacaat tacgagtgac gagtcggtca          240
gatagaagga tctagaaaag caagtcgtcg ctatataact aagggatccg tcacggaagg          300
atctagaaac cctagtagtg aaccctctct ataaaacctc ttccttcttt cattcggtgc          360
ctattcccat tttcttcctc taaaccctaa acaactcttt ctcttcttcc ttcgctcgtc          420
gttctccctc gcgtagatcg a                                                    441

```
<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cacgcgtttg gagatgactg atttatctta ggaatg                              36

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cacgcgtaac aattacgagt gacgagtc                                       28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacgcgtcgc tatataacta agggatcc                                       28

<210> SEQ ID NO 20
<211> LENGTH: 627
<212> TYPE: DNA
<213> ORGANISM: Glycine max

<400> SEQUENCE: 20
gtttggagat gactgattta tcttaggaat ggtatgattt gtattacttt ggtaaatatt    60
ttgacataca ttatttgtgt aattttttttt atgtttgagt taaaaagact ccccatatag  120
ttaggttcct agtcaatcat ttgtggttgg ttttggtaaa tactactgat gagttattta  180
ttttttaaaa aataaagacg aggatttgaa atttagaata agattagatc tacaaaattt  240 attttttataa agacagagtt aaagatttat tactgataaa aaaaaaaaag aagaggattt  300
gaaatttaga acaagattag attggtgtaa cgtgaaccac gcgatgttga ttactatttt  360
acattagaat gttaattttt aggcgaagcc ggcttaacgt aacaattacg agtgacgagt  420
cggtcagata gaaggatcta gaaaagcaag tcgtcgctat ataactaagg gatccgtcac  480
ggaaggatct agaaacccta gtagtgaacc ctctctataa aacctcttcc ttctttcatt  540
cggtgcctat tcccattttc ttcctctaaa ccctaaacaa ctctttctct tcttccttcg  600
ctcgtcgttc tccctcgcgt agatcga                                       627

<210> SEQ ID NO 21
<211> LENGTH: 230
<212> TYPE: DNA
<213> ORGANISM: Glycine max

<400> SEQUENCE: 21
cgtaacaatt acgagtgacg agtcggtcag atagaaggat ctagaaaagc aagtcgtcgc    60
tatataacta agggatccgt cacggaagga tctagaaacc ctagtagtga accctctcta  120
```

```
taaaacctct tccttctttc attcggtgcc tattcccatt ttcttcctct aaaccctaaa      180
caactctttc tcttcttcct tcgctcgtcg ttctccctcg cgtagatcga                230

<210> SEQ ID NO 22
<211> LENGTH: 176
<212> TYPE: DNA
<213> ORGANISM: Glycine max

<400> SEQUENCE: 22
cgtcgctata taactaaggg atccgtcacg gaaggatcta gaaaccctag tagtgaaccc       60
tctctataaa acctcttcct tctttcattc ggtgcctatt cccatttct tcctctaaac      120 cctaaacaac tctttctctt cttccttcgc tcgtcgttct ccctcgcgta gatcga          176
```

HIGHLY ACTIVE SOYBEAN PROMOTER FROM THE SUBI-3 POLYUBIQUITIN GENE AND USES THEREOF

CROSS-REFERENCE TO RELATED APPLICATIONS

This application claims the benefit of the PCT/US2008/005972 filed May 8, 2008, which claims priority to the United States Provisional Application No. 60/928,212, filed May 8, 2007, the disclosure of which is incorporated herein by reference.

This invention was not made with government support and the government has no rights in this invention.

STATEMENT REGARDING FEDERALLY SPONSORED RESEARCH

This invention may have been made with government support and the government may have rights in this invention.

TECHNICAL FIELD AND INDUSTRIAL APPLICABILITY OF THE INVENTION

This invention relates to plant promoters, in particular to soybean promoters and fragments thereof and their use in altering expression of at least one heterologous nucleic acid fragment in plants.

This invention also relates to a method for quantifying gene expression using an automated image collection and analysis system, in particular, by tracking and quantifying transient gene expression using time-lapse animations of tissue growth and gene expression.

BACKGROUND OF THE INVENTION

In the context of this disclosure one or more of the following terms may be used.

Promoter analysis in plants can provide information on both the strength of the promoter and its regulation in different tissues. Promoter analysis studies have been performed with either stably-transformed tissues or using transient expression analyses. For stable transformation, the time required for generation of a transgenic plant can be as short as six weeks (An et al. 1986), but can often extend beyond five months when transformation and plant recovery is slow (Santarém and Finer 1999). Production of stably-transformed plants is necessary for a detailed examination of promoter expression; however, quantification of promoter strength and comparative analyses in stably transformed plants can still be difficult due to variation in transgene expression among transgenic clones (Finnegan and McElroy 1994).

Rapid, quantifiable, and reproducible promoter analyses are simplified using transient expression, where gene expression can be observed in as little as 1.5 hours post introduction (Ponappa et al. 1999) and gene expression will not be influenced by copy number or site of integration. Transient expression analysis can be performed via direct DNA introduction into protoplasts using electroporation (Christensen et al. 1992) or PEG (Hartmann et al. 1998), or particle bombardment-mediated transformation into intact plant tissues (Rolfe and Tobin 1991). Agroinfiltration of tobacco (Bendahmane et al. 1999; Vaucheret, 1994) is also commonly used for rapid analysis of transgene effects. Reporter genes such as luciferase (Ow et al, 1986), β-*glucuronidase* (Samac et al. 2004; Vain et al. 1996) and chloramphenicol acetyl transferase (Kang et al. 2003) are most commonly utilized for quantification of promoter activity. Unfortunately, visualization of luciferase and β-glucuronidase activity requires the addition of an artificial substrate and quantification of promoter activity using all of these reporter genes and requires the extraction of protein from the sample, destroying the sample and eliminating the ability to follow gene expression in the same piece of tissue over time.

The green fluorescent protein (gfp) gene offers tremendous opportunities for promoter analysis in plants since its expression can be followed in the same piece of tissue over extended periods of time (Piston et al. 1999). Although GFP expression has been used in studies to characterize promoter activity (Abebe et al. 2006), reports on the quantification of GFP expression using image analysis (Nagatani et al. 1997), spectofluorometry (Richards et al. 2003) or fluorescence spectroscopy (Stewart et al. 2005) are minimal.

Standard methods are needed for the evaluation of promoter strength based on GFP detection. Recently, an automated robotics system was developed for monitoring GFP expression over time in multiple pieces of tissue (Buenrostro-Nava et al. 2005). The robotics system consisted of a 2-dimensional robotics platform, a cooled CCD camera, and a dissecting fluorescence microscope, all under computer control. Although the monitoring system was initially used for automated image collection of GFP expression in stably-transformed somatic embryos (Buenrostro-Nava et al. 2006) and Agrobacterium (Buenrostro-Nava et al. 2003), it also has utility for rapid quantification of promoter strength using transient expression analyses.

Soybean (*Glycine max* (L.) Merr.), a valuable agronomic crop world-wide, has the highest transgenic acreage of any crop. As efforts move forward to produce new and improved transgenic soybean, the need for different types of native soybean promoters will continue to increase. Some soybean promoters have already been identified but these promoters direct expression in a tissue-specific (Chen et al. 1986) or inducible manner (Czarnecka et al. 1989; Liu et al. 1994). A strong, constitutive, native soybean promoter, which could replace the constitutive Cauliflower Mosaic Virus 35S (CaMV35S) was sought. Of the strong constitutive plant promoters that have been used extensively for directing transgene expression, the polyubiquitin promoters have received the most widespread attention (Christensen and Quail 1996). A common feature of polyubiquitin promoters is the presence of a leading intron, which is considered part of the promoter, and can influence transgene expression (Christensen and Quail 1996). Removal of the intron from the promoter region either reduces the strength of the promoter (Plesse et al. 2001) or results in complete loss of promoter activity (Wang and Oard 2003).

In addition to a strong constitutive promoter, a developmentally regulated promoter would be useful for comparative studies. Although soybean promoters active during late stages of seed development are available (Chen et al. 1986), EST data from induced soybean somatic embryos (Thibaud-Nissen et al. 2003) now permits the identification of useful early embryo-specific promoters.

SUMMARY OF THE INVENTION

In one aspect, there is provided a constitutive *Glycine max* polyubiquitin (Gmubi) promoter and an early embryo-specific *Glycine max* heat shock protein 90-like (GmHSP90L) promoter that were isolated, fused to the gfp coding region, and introduced into cotyledonary tissue of lima bean for rapid evaluation of promoter activity using automated image collection and analysis.

In another aspect, promoters from soybean have been identified and characterized which regulate or control expression of an introduced marker gene in soybean. Based on microarray expression data, the 5' regulatory regions from different genes have been recovered to yield different promoters. The promoters have been additionally modified by truncation and fusion with other promoter/regulatory regions to generate an array of promoters with different intensities and specificities of expression. In one embodiment, one of the soybean promoters shows much higher constitutive expression than the CaMV35S promoter, which is a promoter standard. Other promoters show root-specific expression, while some appear to express only in early-staged embryos.

These promoters are useful for regulating transgene expression. They are native soybean promoters or "hybrid" promoters that were produced by fusion of two different native promoters. Some of the promoters yield high expression levels which is desired for some transgenes while others appear to drive expression in the roots, which are useful for expression of a gene for pathogen resistance where root tissue is targeted by the pathogen. The promoters have been characterized using the green fluorescent protein using both transient expression and stable expression data.

In another broad aspect, there is provided herein a method for evaluating promoters, based on intensity of expression of the green fluorescent protein using an automated image collection and analysis system. The method allows for the generation of quantitative data on promoter strength, using a transient expression system, as well as expression in stably transformed tissues.

The method described herein also provides for the capability to track and quantify gfp gene expression in plant tissues, over time.

In a broad aspect, there is provided herein a process for expressing nucleic acids in transgenic plants under the control of a soybean ubiquitin promoter.

In another broad aspect, there are provided novel soybean ubiquitin promoters, or to a functional equivalent or equivalent fragment which has essentially the same promoter activity as said promoters.

In still another broad aspect, there are provided herein novel nucleic acid constructs for stable transgenic expression of nucleic acids comprising at least one promoter as described herein. Also provided herein are vectors comprising such nucleic acid constructs.

In yet another broad aspect, there in provided herein transgenic plants, plant tissues and/or seeds transformed with the promoters and/or nucleic acid constructs as described herein.

In still another broad aspect, there are provided herein isolated nucleic acid molecules comprising at least one soybean promoter as set forth in the sequences disclosed herein.

Various objects and advantages of this invention will become apparent to those skilled in the art from the following detailed description of the preferred embodiment, when read in light of the accompanying drawings.

BRIEF DESCRIPTION OF THE DRAWINGS AND SEQUENCES

The patent or application file contains at least one drawing executed in color. Copies of this patent or patent application publication with color drawing(s) will be provided by the Office upon request and payment of the necessary fee.

The invention can be more fully understood from the following detailed description, the drawings and the Sequence Descriptions that form a part of this application. The sequence descriptions and Sequence Listing attached hereto comply with the rules governing nucleotide and/or amino acid sequence disclosures in patent applications as set forth in 37 CFR §§1.821-1.825. The Sequence Descriptions contain the three letter codes for amino acids as defined in 37 CFR §§1.821-1.825, which are incorporated herein by reference.

FIG. 1. Maps of promoter constructs used for particle bombardment-mediated DNA introduction into lima bean cotyledons. All the promoters were positioned 5' to the GFP open reading frame.

Gmubi: full length *Glycine max* ubiquitin promoter with an intronic sequence Gmupri: *Glycine max* ubiquitin pre-intronic promoter contained only the nucleotides before the putative intronic sequence.

GmHSP90L: *Glycine max* heat shock protein 90-like, with promoter truncations leading to promoter sizes of 177, 231, 443, 628, and 830 nucleotides.

CaMV35S: the full-length Cauliflower Mosaic Virus 35S promoter. All numbers are in relation to the translational start of the gfp coding sequence.

FIG. 2. Examples of images collected 24 h post-bombardment with Gmubi, Gmupri, and CaMV35S promoter constructs. The computed values for these single images are shown in the accompanying table.

FIG. 3. Expression profiles of Gmubi, Gmupri, and CaMV35S promoters were calculated from replicated (n=6) series of images for each promoter. The Total Expression calculation is described in the materials and methods. Focus Number was the number of foci expressing GFP in the same area used for Total Expression determinations.

FIG. 4. Expression profiles of GmHSP90L promoter constructs: 177, 231, 443, 628, and 830. Quantification as described in FIG. 3 (n=9).

FIGS. 5A-B Gmubi Promoter [SEQ ID NO: 1].

FIGS. 6A-B 1500Gmubi [SEQ ID NO: 2].

FIGS. 7A-B Gmupri (Gmubi pre-intronic) Promoter [SEQ ID NO: 3].

FIGS. 8A-B Gmucor (Minimal) Promoter [SEQ ID NO: 5].

FIGS. 9A-B Gmactin Promoter [SEQ ID NO: 7].

FIGS. 10A-B GmS11 Promoter [SEQ ID NO: 10].

FIGS. 11A-F GmHSP90L Promoters and derivatives: GmHSP90L-830 Promoter is shown in FIG. 11B [SEQ ID NO: 15]; GmHSP90L-628 Promoter is shown in FIG. 11C [SEQ ID NO: 20]; GmHSP90L-443 Promoter is shown in FIG. 11D [SEQ ID NO: 16]; GmHSP90L-231 Promoter is shown in FIG. 11E [SEQ ID NO: 21]; GmHSP90L-177 Promoter is shown in FIG. 11F [SEQ ID NO: 22].

FIG. 17 contains a table showing soybean promoter GFP stable events.

FIG. 18 contains a table showing tissue-specific expression.

Figure 19:
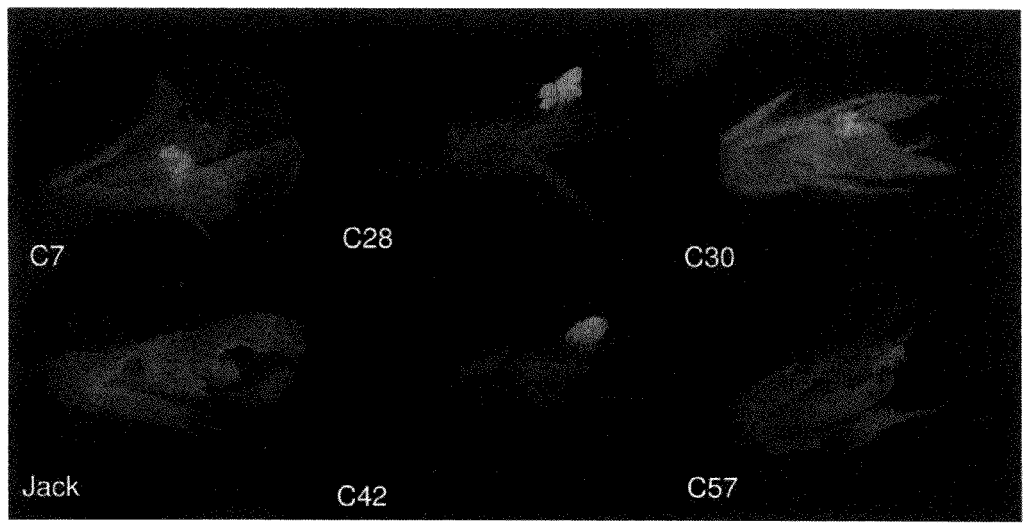

FIG. 19 contains photographs of the following clones: C7, C28, C30, C42, C57, and Jack, showing that Gmupri was express in pollen.

Figure 20A:
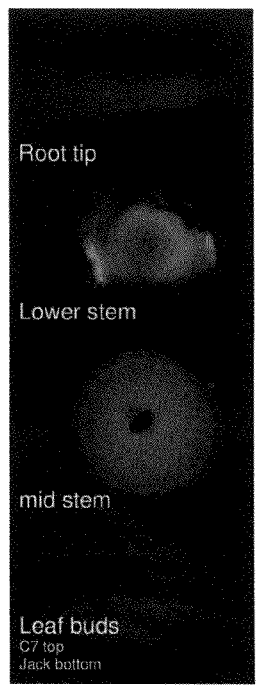
Figure 20B:
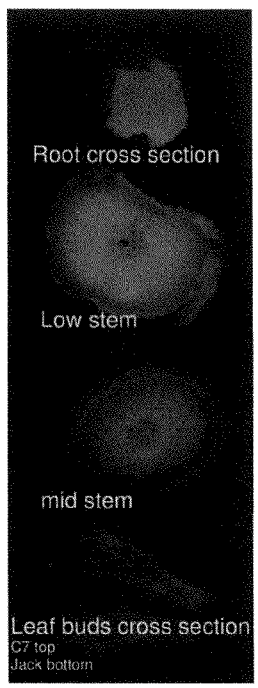
Figure 20C:
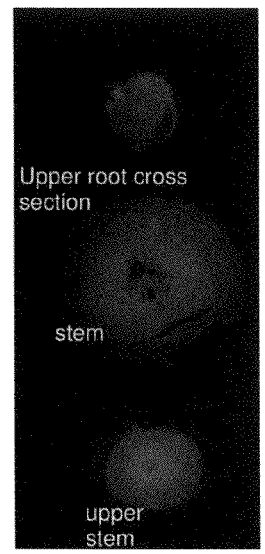

FIGS. 20A-20C are photographs showing GFP expression in a Gmupri C7 plant, specifically in the root tip, the lower stem, mid stem and leaf buds.

Figure 21:
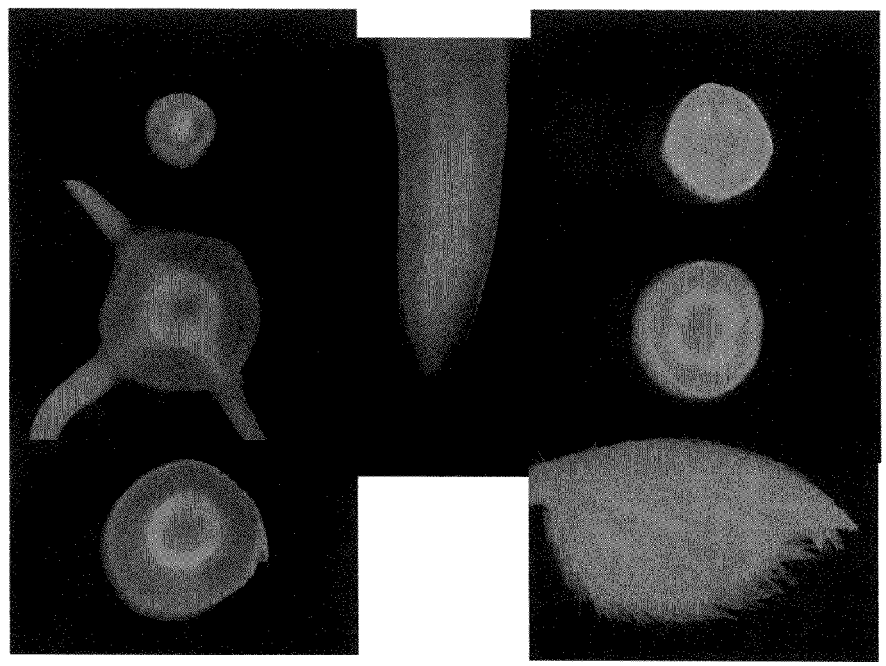

FIG. 21 is a photograph showing GFP expression in a Gmubi C72 seedling at 4 days.

Figure 22:
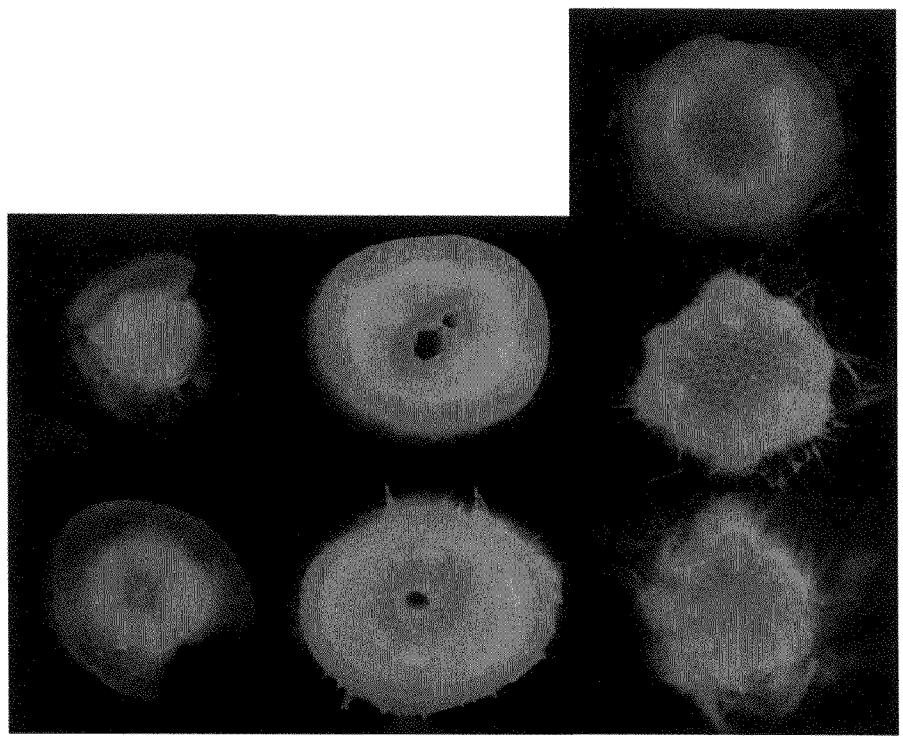

FIG. 22 is a series of photographs showing GFP expression in a Gmubi C72 plantlet from bottom to top, i.e., from root through stem.

Figures 23A, 23B, 23C:
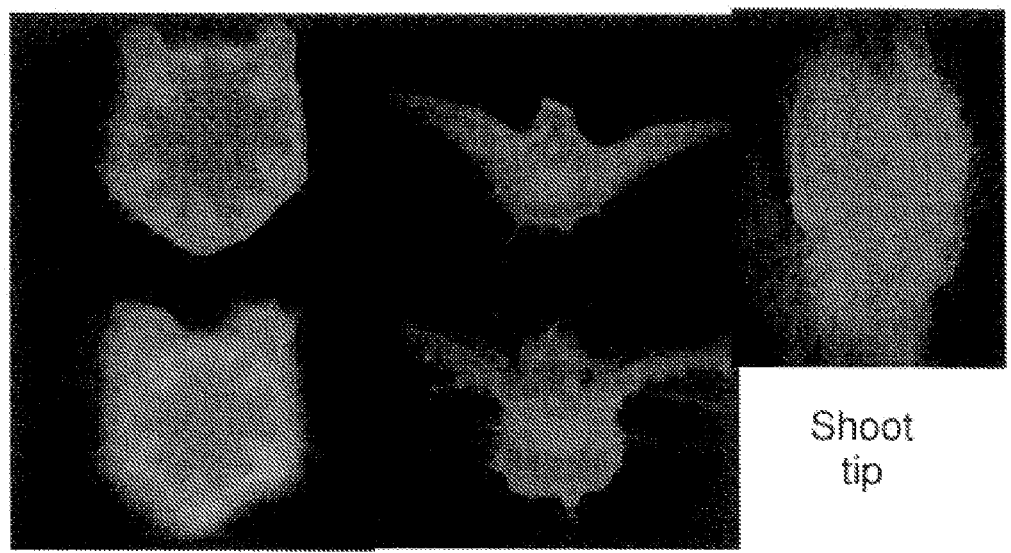

FIGS. 23A-23C are photographs showing GFP expression in a Gmubi C72 plantlet in the petiole (FIG. 23A), the leaf (FIG. 23B), and the shoot tip (FIG. 23C).

Figure 24:
Figure 25A:
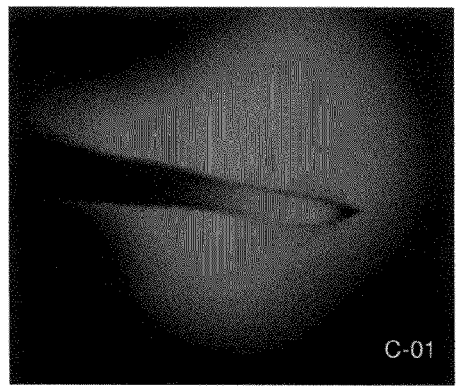
Figure 25B:
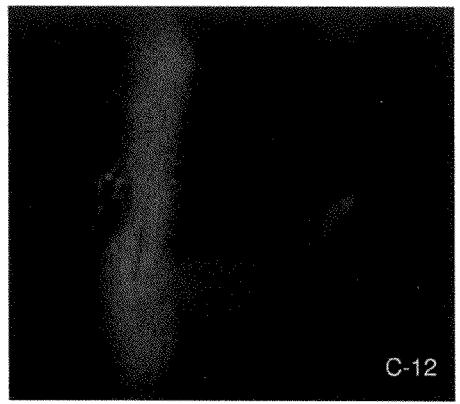
Figure 25C:
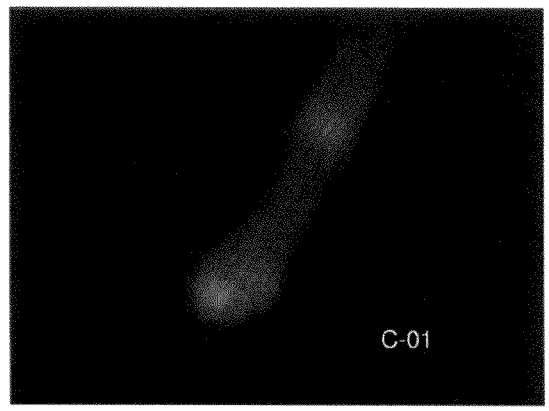
Figure 25D:
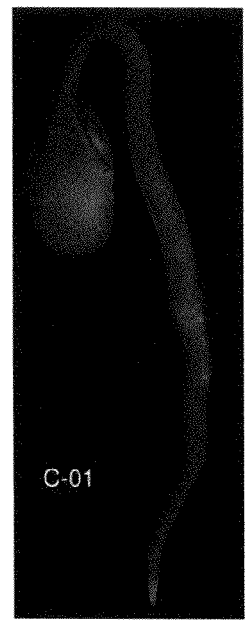

FIG. 24 is a photograph showing GFP expression in pollen in a Gmubi C72 clone.

FIGS. 25A-25D are photographs showing GFP expression in GmS11 clones: C-01 shown in FIGS. 25A, 25C and 25D; and C-12 shown in FIG. 25B.

FIGS. 26A and 26B are blots showing: in FIG. 26—Bgl II digest—no sited in either vector; and FIG. 26B showing Nhe I digest—single site in GFP vector.

Figure 27A:
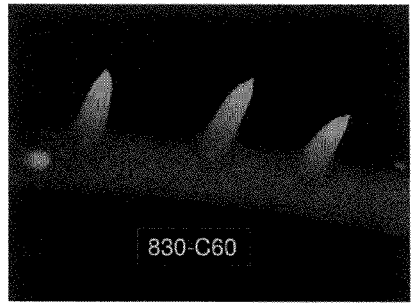
Figure 27B:
Figure 27C:
Figure 27D:

FIGS. 27A-27D are photographs showing GFP expression in HSP90L seedlings for the following clones: HSP830-C60 (FIG. 27A); HSP830-C48 (FIG. 27B); HSP443-055 (FIG. 27C); and HSP830-C48 (FIG. 27D).

Figure 28A:
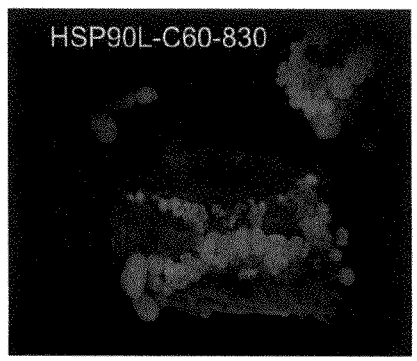
Figure 28B:
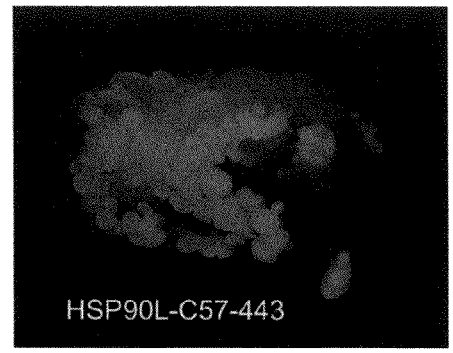
Figure 28C:
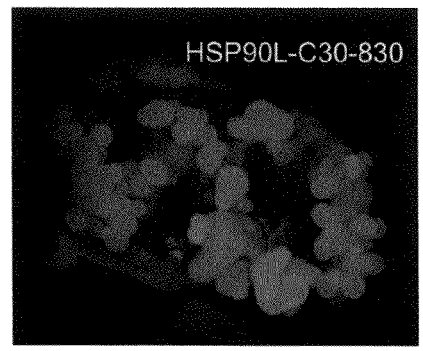

FIGS. 28A-28C are photographs showing HSP90L embryo induction for the following clones: HSP90L-C60-830 (FIG. 28A); HSP90L-C57-4480 (FIG. 28B); and HSP90L-C30-830 (FIG. 28C).

DETAILED DESCRIPTION OF THE PREFERRED EMBODIMENT(S)

The present invention relates to isolated nucleic acid molecules and their corresponding encoded polypeptides able to confer the desired traits or to prevent undesired traits in plants. The present invention further relates to the use of these nucleic acid molecules and polypeptides in making transgenic plants, plant cells, plant materials or seeds of a plant having such modulated growth or phenotype characteristics that are altered with respect to wild type plants grown under similar conditions.

In the context of this disclosure, one or more of the following definitions may be used.

An "isolated nucleic acid fragment" refers to a polymer of ribonucleotides (RNA) or deoxyribonucleotides (DNA) that is single- or double-stranded, optionally containing synthetic, non-natural or altered nucleotide bases. An isolated nucleic acid fragment in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. Examples of suitable sets of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above, except for the temperature of the final two 30 min. washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%, such as 81%, 82%, 83%, 84%, 85%, 86%, 87%, 88%, 89%, 90%, 91%, 92%, 93%, 94%, 95%, 96%, 97%, 98% and 99%.

A "substantially homologous sequence" refers to variants of the disclosed sequences such as those that result from site-directed mutagenesis, as well as synthetically derived sequences. A substantially homologous sequence of the present invention also refers to those fragments of a particular, promoter nucleotide sequence disclosed herein that operate to promote the seed-preferred expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription; RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. Functional RNA is including, but not limited to, transfer. RNA (tRNA) and ribosomal RNA (rRNA). The promoter sequence consists of proximal and more distal upstream elements, the latter elements often referred to as enhancers.

Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity. An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA.

Messenger RNA" ("mRNA") refers to RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded by using the klenow fragment of DNA polymerase I.

"Sense" RNA refers to RNA transcript that includes mRNA and so can be translated into protein within a cell or in vitro.

"Antisense RNA" refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence.

"Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product e.g., a mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein.

"Antisense inhibition" refers to the production of antisense RNA transcripts capable of suppressing the expression of the target protein.

"Overexpression" refers to the production of a gene product in transgenic organisms that exceeds levels of production in normal or non-transformed organisms.

"Co-suppression" refers to the production of sense RNA transcripts capable of suppressing the expression or transcript accumulation of identical or substantially similar foreign or endogenous genes.

The mechanism of co-suppression may be at the DNA level (such as DNA methylation), at the transcriptional level, or at post-transcriptional level.

"Antisense inhibition" refers to the production of antisense RNA transcripts capable of suppressing the expression of the target protein.

"Hairpin" structures refers to structures that incorporate all, or part, of an mRNA encoding sequence in a complementary orientation that results in a potential "stem-loop" structure for the expressed RNA. This increases the frequency of co-suppression in the recovered transgenic plants. Another variation describes the use of plant viral sequences to direct the suppression, or "silencing", of proximal mRNA encoding sequences "Suppression" refers to a reduction of the level of enzyme activity or protein functionality (e.g., a phenotype associated with a protein) detectable in a transgenic plant when compared to the level' of enzyme activity or protein functionality detectable in a non-transgenic or wild type plant with the native enzyme or protein.

The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms.

Standard recombinant DNA and molecular cloning techniques used herein are well known in the art and are described more fully in Sambrook, J. et al., In Molecular Cloning: A Laboratory Manual; 2ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments which consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

A "recombinant expression construct" is a plasmid vector or a fragment thereof comprising the instant soybean seed-specific promoters. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression, and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

The invention of the present application may be described by, but not necessarily limited to, the following exemplary embodiments.

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

With the increasing amount of information available from genomics data and microarray analyses, functional analyses of genes has become high priority for many laboratories. Along with gene expression profiles, characterization of the promoters which regulate those genes is also of significant value.

Promoter analyses can be performed using either transient or stable expression studies. For transient expression studies, gene introduction is immediately followed by quantification of gene expression, usually following extraction of analyzed components. Expression analyses in stably transformed tissues requires the production of stably transformed plant tissues and is usually more precise.

Therefore, in a first aspect, there is provided herein a method which uses robotics and image analysis in order to gather data such as high throughput, rapid analysis of gene expression in living plant tissues. Robotic tracking of numerous samples for image collection allows multiple samples to be tracked over time with minimal variation in illumination and sample positioning. In a particular aspect, a robotics tracking system has been developed for semi-continual monitoring of gfp gene expression.

As described herein, different forms of different soybean promoters were isolated, fused to the GFP coding region and analyzed using both transient and stable expression.

For transient expression studies, promoter fusions were introduced directly into cotyledonary tissues of lima bean for rapid evaluation of promoter activity.

For stable expression studies, promoter constructions were introduced into embryogenic soybean cultures via particle bombardment.

Promoter Isolation: A soybean (*Glycine max*) ubiquitin promoter was amplified from genomic DNA as either a full length fragment (Gmubi) or a truncated form, without putative intronic sequences (Gmupri). Primers were designed, based on GenBank® submission D28123 (*Glycine max*) SUBI-3 gene for ubiquitin.

A soybean extensin promoter (Soybean Root Promoter, SRP) was amplified from genomic DNA based on GenBank® submission AF520576. The soybean Actin and HSP90 promoters were recovered using the GenomeWalker™ System and the 5' sequence of early embryo-specific ESTs, identified from microarray data. Five different fragments of the HSP90-like promoter were generated and fused to the gfp coding region. Promoters were compared to a 35S promoter for timing and intensity of expression.

Transient Expression: Cotyledons from germinating lima bean (*Phaseolus lunatus*) seedlings were excised and bombarded with the various promoter constructions. Cotyledons were placed on top of a baffle, to allow air flow around the sample and minimize tissue displacement. Cotyledons were placed, flat side up, on media in Petri dishes with multiple cotyledons per dish. GFP expression was recorded and tracked every hour for approximately 100 hours using an automated image collection system that included a dissecting microscope, a digital camera and a 2 dimensional robotics platform, all under computer control. Following image collection, GFP expression was quantified using ImageJ software.

Stable Expression: Stably-transformed soybean tissues were generated following particle bombardment of embryogenic cultures. Promoter constructions were co-introduced with a selectable marker for hygromycin resistance and plants were regenerated from selected clones. Proliferative embryogenic tissues and various transgenic plant parts were evaluated for gfp expression.

As shown in the examples herein, the pre-intronic version (Gmupri) yielded lower expression. The presence of the intron appears to enhance transient expression. The overall GFP intensity, number of foci and intensity per focus can be used as valid measures of promoter strength. As apparent regulatory elements were eliminated from the HSP90-like promoter, activity declined in a stepwise fashion. The size of the promoter itself was not directly proportional to promoter activity.

The level and timing of peak GFP expression provided some early clues to the characteristics of different isolated promoters. Expression in proliferative embryogenic D20 tissue was variable; no promoters were truly constitutive. The Gmubi and 35S promoters were the most active, with higher expression with Gmubi. Actin and HSP90 were active in very young embryogenic tissues. Gmupri-driven GFP expression was more pronounced in older embryogenic tissues. GFP was most easily detected in root tissues and all promoters displayed some level of activity in roots. Observation of expression in whole plants may have been masked somewhat by chlorophyll autofluorescence.

In a broad aspect, there is provided herein a novel automated image collection and analysis system that is used to compare two new soybean (*Glycine max* (L.) Merr.) promoters with the cauliflower mosaic virus 35S (CaMV35S) promoter, which was used as an expression standard. For expression comparisons, various permutations of a soybean polyubiquitin (Gmubi) promoter, a soybean heat shock protein 90-like (GmHSP90L) promoter and the CaMV35S promoter were placed upstream of a green fluorescent protein (gfp) gene. DNA constructs were introduced via particle bombardment into excised cotyledons of germinating lima bean (*Phaseolus lunatus* L.) seeds, which were arranged in Petri dishes for automated image capture and image analysis.

The automated system allows monitoring and quantification of gfp gene expression in the same piece of tissue over time. The Gmubi promoter, with its intronic region intact, showed the highest expression that was over 5-times stronger than the CaMV35S promoter. When an intronic region was removed from the Gmubi promoter, GFP expression was reduced, but was still over 2-times greater than with the CaMV35S promoter. The full-length soybean GmHSP90L promoter was 4-times stronger than the CaMV35S promoter. Truncation of the GmHSP90L promoter resulted in stepwise decreases in promoter strength, which appear to correspond to removal of regulatory elements. Automated image capture and analysis allowed the rapid and efficient evaluation of these new promoters.

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques and can be introduced into the plant species of interest by, for example, Agrobacterium-mediated transformation, or by other means of transformation.

Thus, in a particular aspect, there is described herein a process for expressing nucleic acids in transgenic plants under the control of a soybean ubiquitin promoter, wherein the process comprises the following steps: linking a nucleic acid to be expressed to a promoter containing at least one of the sequences coding: Gmubi Promoter [SEQ ID NO: 1]; 1500Gmubi [SEQ ID NO: 2]; Gmupri (Gmubi pre-intronic) Promoter [SEQ ID NO: 3]; Gmucor (Minimal) Promoter [SEQ ID NO: 5]; Gmactin Promoter [SEQ ID NO: 7]; GmS11 Promoter [SEQ ID NO: 10]; GmHSP90L-830 Promoter [SEQ ID NO: 15]; GmHSP90L-628 Promoter [SEQ ID NO: 20]; GmHSP90L-443 Promoter [SEQ ID NO: 16]; GmHSP90L-231 Promoter [SEQ ID NO: 21]; GmHSP90L-177 Promoter [SEQ ID NO: 22]; or to a functional equivalent or equivalent fragment which has essentially the same promoter activity as said promoter, to form a construct; and introducing into a plant the construct under conditions which enable the nucleic acid to be stably integrated into the genome of said plant.

The nucleic acid to be expressed can be functionally linked to one or more further regulatory sequences. The nucleic acid can encode a gene selected from the group consisting of a selection marker, a reporter gene, an enzyme, a protein which mediates resistance to insects, viruses, bacteria, fungi or nematodes, a nucleic acid sequence or a protein which mediates in plants resistance to drought, cold, heat or salt, an inhibitor, a lectin, an RNAase, a ribozyme, an antibody, a vaccine, a pharmaceutical, an anti-freezing protein, a cytochrome P-450 protein, a transcription activator or repressor. It is also possible to introduce advantageously metabolic genes into plants, to enable particular products and by-products of naturally occurring metabolic processes to be utilized for a wide range of industries, including the feed, food, cosmetics and pharmaceutical industries. These molecules which are collectively referred to as "fine chemicals" include, for example, vitamins, amino acids, carbohydrates or lipids and fatty acids. Also, the construct can contain one or more further genes under the control of the soybean ubiquitin promoter or of another promoter.

The nucleic acid can be expressed in the sense or antisense direction or in the sense and antisense directions. The nucleic acid construct can be inserted between two T-DNA sections. The nucleic acids can be expressed constitutively.

The transgenic plant can be a monocotyledonous or dicotyledonous plant. Non-limiting examples of monocotyledonous plants include barley, corn, grass, millet, oats, rice, rye, triticale, and wheat. Non-limiting examples of dicotyledonous plants include: alfalfa, almond, *Arabidopsis*, avocado, bay, borage, calendula, canola, carrot, castor-oil plant, cocoa, coconut, coffee, cotton, eggplant, evening primrose, hazelnut, hemp, linseed, macadamia, manioc, mustard, oil palm, oilseed olive, pea, peanut, pepper, pistachios, poplar, poppy, potato, pumpkin, punica, rape, safflower, sesame, soybean, sugar beet, sunflower, tagetes, tea, thistle, tobacco, tomato, verbascum, walnut, and wild roses.

In certain embodiments, the products produced in the transgenic plants are due to expression of the nucleic acid isolated after culturing of the plant.

In a particular aspect, a nucleic acid construct for stable transgenic expression of nucleic acids can include: a promoter containing the desired promoter sequence, or one or more functional equivalents or equivalent fragments of the promoter, which have essentially the same promoter activities as the promoter, where the promoter is functionally linked to a nucleic acid sequence to be expressed transgenically. The nucleic acid construct can include at least one further element such as: a) a nucleic acid sequence to be expressed being functionally linked to one or more further genetic control sequences; b) a nucleic acid construct comprising one or more additional functional elements; c) a polylinker located between the promoter and the nucleic acid sequence to be expressed; or d) a nucleic acid construct comprising at least one further nucleic acid under the control of a promoter containing the sequence, or of a functional equivalent or equivalent fragment thereof, or of another promoter.

In another aspect, there are provided herein vectors that include the nucleic acid construct of the promoter sequences described herein.

In another aspect, there are provided herein transgenic plants, transformed with the nucleic acid construct described herein.

In another aspect, there are provided herein methods for preparing foodstuffs, feedstuffs, seeds, cosmetics, pharmaceuticals or fine chemicals comprising the transgenic plant as described herein.

The present invention is further defined in the following Examples, in which parts and percentages are by weight and degrees are Celsius, unless otherwise stated. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; 2.sup.nd ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. All publications, including patents and non-patent literature, referred to in this specification are expressly incorporated by reference herein.

EXAMPLES

Materials and Methods

Plasmid Constructs

Figure 1:
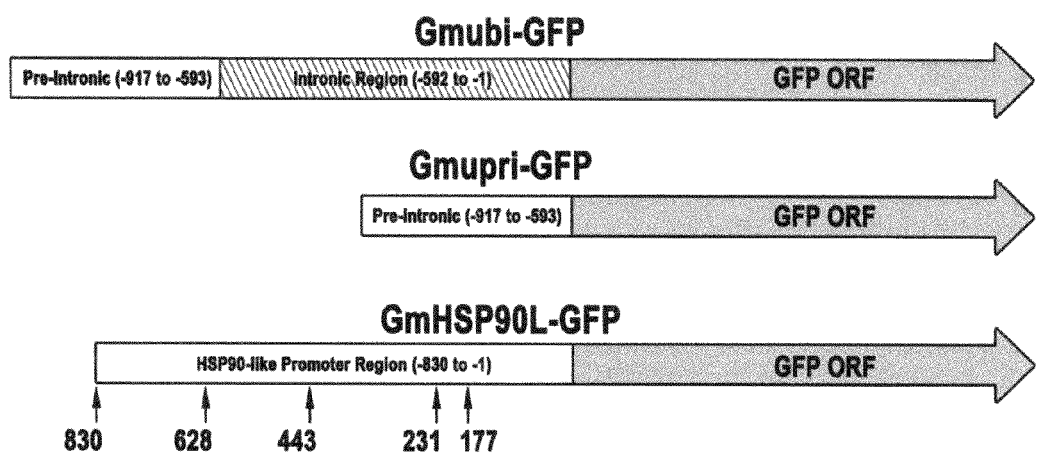

Eight different promoter constructs were generated (FIG. 1). All promoters were placed upstream of a modified gfp gene (sGFP(S65T); Chiu et al. 1996). Two different forms of a soybean (*Glycine max*) polyubiquitin promoter were evaluated, along with 5 different forms of a soybean heat shock protein 90-like (GmHSP90L) promoter. The CaMV35S promoter was used as a standard.

The soybean (*Glycine max*) polyubiquitin promoter (Gmubi) was identified from GenBank submission D28123 (*Glycine max* SUBI-3). Based on similar motifs in this gene's 5' region and those found in the maize polyubiquitin 1 promoter (Christensen et al. 1992; Ling et al. 1995), primers were designed to clone the entire 5' UTR region of the D28123 sequence, adding a 5' SphI site and a 3' BamHI site to allow insertion of the promoter in front of the gfp gene.

The entire 5' Gmubi fragment was amplified from soybean genomic DNA using the FailSafe™ PCR system (Epicentre Biotechnologies, Madison, Wis.). An intron-less version of the Gmubi promoter (Gmupri; *Glycine max* pre-intronic) was recovered by amplifying the 328 by segment of Gmubi preceding the intron, adding a 5' SphI site and a 3' BamHI site as before. This fragment was amplified directly from the Gmubi promoter fragment and was also inserted in front of the gfp gene.

The GmHSP90L promoter was selected based on early embryogenesis expression data from EST-based microarrays (Thibaud-Nissen et al. 2003). A GenomeWalker™ (Clontech, Palo Alto, Calif.) library was constructed from soybean genomic DNA according to the manufacturer's instructions. Nested reverse primers were constructed against the GmHSP90-like EST (AW278784) at the junction between the 5' UTR and the start of the open reading frame. The first-round primer was complementary to a segment just inside the open reading frame. The secondary primer was designed to be complementary to the 3' end of the upstream 5' UTR and the junction of the 5' UTR with the start codon, but with modifications of the sequences overlapping the start codon to create an NcoI site encompassing the ATG. This allowed transcriptional fusion of the promoter directly to the gfp open reading frame. All the primers used in cloning the promoter regions are shown herein.

Plant Material

All 8 promoter constructs were assayed using a newly-developed bean cotyledon transient assay system. Cotyledonary tissue from germinating lima bean (*Phaseolus lunatus* L. cv. "Henderson-Bush") seeds was targeted for DNA introduction. Lima bean seed source plants were grown in the greenhouse (16/8h light:dark, 28° C.) with supplemental lighting from high pressure sodium lamps. Mature seeds, used in these experiments, were harvested and stored at room temperature for up to 4 weeks prior to use.

For germination, seeds were sterilized with a 10% bleach solution for 20 minutes and rinsed 5 times with sterile deionized water. Sterilized seeds were placed in Magenta GA7 containers between layers of a folded white paper towel that was saturated with 25 mL of sterile water. After 4 days (40 $\mu Em^{-2}s^{-1}$; 16/8h light:dark, 25° C.), the light-green cotyledons were excised from the germinating seedlings and placed in Petri dishes containing OMS medium (pH 5.7), which consisted of MS salts (Murashige and Skoog 1962), B5 vitamins (Gamborg et al. 1968), 3% sucrose and 0.2% Gelrite™ (Aceto Corporation; Lake Success, N.Y.).

DNA Introduction

Cotyledons were placed, adaxial surface up, on top of an inverted modified baffle, which was comprised of a 500 µm nylon screen melted to the bottom of a 400 ml polypropylene beaker (Finer et al. 1992) with triangular slots cut in the bottom to allow expelled helium gas to flow around the sample and minimize tissue displacement. Each DNA construct was precipitated onto tungsten particles and introduced into the target tissue using the Particle Inflow Gun as described previously (Finer et al. 1992). Following the introduction of each DNA construct, cotyledons were immediately placed adaxial side up in Petri dishes containing OMS medium.

Gmubi, Gmupri, and CaMV35S promoter constructs were bombarded in two independent experiments of 3 replicates each. The GmHSP90L constructs were bombarded in three independent experiments of 3 replicates each.

Image Collection and Analysis

Once GFP expression was detected (1-3 hours), the Petri dishes were placed on the robotics platform of the automated image collection system (Buenrostro-Nava et al. 2006) which consisted of a MZFLIII dissecting microscope (Leica, Heerbrugg, Switzerland) equipped with a GFP2 filter set (Ex. 480±40 nm; Em. 510 nm LP), a Spot-RT CCD digital camera (Diagnostic Instruments Inc., Sterling Heights, Mich.), and a 2-dimensional robotics platform (Arrick Robotics Inc., Hurst, Tex.), all under computer control. Images (1600×1200 pixels; 256 gray levels for each of the three channels) of each cotyledon were collected every hour for at least 95 hours. Following image collection, GFP expression was quantified using the software package ImageJ (Rasband 1997-2006). Each series of images was opened, resized to 800×600 pixels, and aligned using the TurboReg plugin (Thevenaz et al. 1998). After alignment, an area comprising 400×300 pixels containing the highest number of expressing cells was cropped from the series of images and used for quantification of GFP.

Each series of images was separated into red, green, and blue channels. Due to background autofluorescence, the contribution of the background to the overall GFP intensity was first subtracted from the entire image. A 20×20 pixel area was selected in the background of the red and green channels (from an area not containing GFP-expressing cells) for determination of background gray value (typically 30-40). The background gray value of the red and green channels was subtracted from every pixel in the respective channel to yield background-corrected images which were used for all expression determinations.

Mean grayscale values in the red and green channels were determined by first segmenting the expressing pixels from the background by adjusting the threshold levels. The mean grayscale values were calculated using only the segmented (expressing) pixels. The "Total Expression" value was calculated by multiplying a mean grayscale value per pixel from the red and green channels by the total number of GFP-expressing pixels in the respective channel and then adding these two values. The green channel was automatically segmented using an entropy threshold algorithm (Sahoo et al. 1988) and the number of GFP-expressing foci was counted.

Results

Target Tissue

Figure 2:
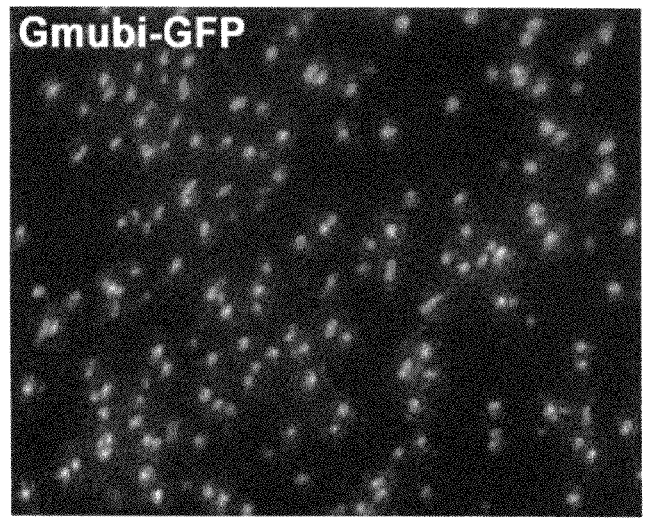

Lima bean cotyledonary tissues showed even and consistent distribution of GFP-expressing foci over much of the adaxial surface of the cotyledons (FIG. 2).

Expression was localized to single targeted cells although very high levels of expression resulted in a low level of reflected fluorescence through adjacent cells. Occasionally, discrete areas of the cotyledon did not show GFP expression, although they were clearly targeted. These patches were either slow to turn green (observed under brightfield conditions) or did not turn green over the course of the experiment, suggesting patches of non-viable or low viability tissues. Similar areas were observed in non-bombarded cotyledons.

Analysis of Gmubi, Gmupri, and CaMV35S Promoters

Although major differences in prOmoter strengths were easily visualized (FIG. 2), quantification of the level of GFP expression provided additional information that was not easily evaluated by the eye alone. Total Expression values were 5-fold greater with the Gmubi promoter compared to the CaMV35S promoter, whereas the Focus Number was only 40% greater. Although the expression levels of GFP driven by the Gmupri promoter appeared to be similar to the expression levels of CaMV35S-regulated GFP based on visual analysis, a 2-fold greater Total Expression value for Gmupri was measured using image analysis. The Focus Numbers obtained for the Gmupri and CaMV35S promoters were not significantly different.

Figure 3:
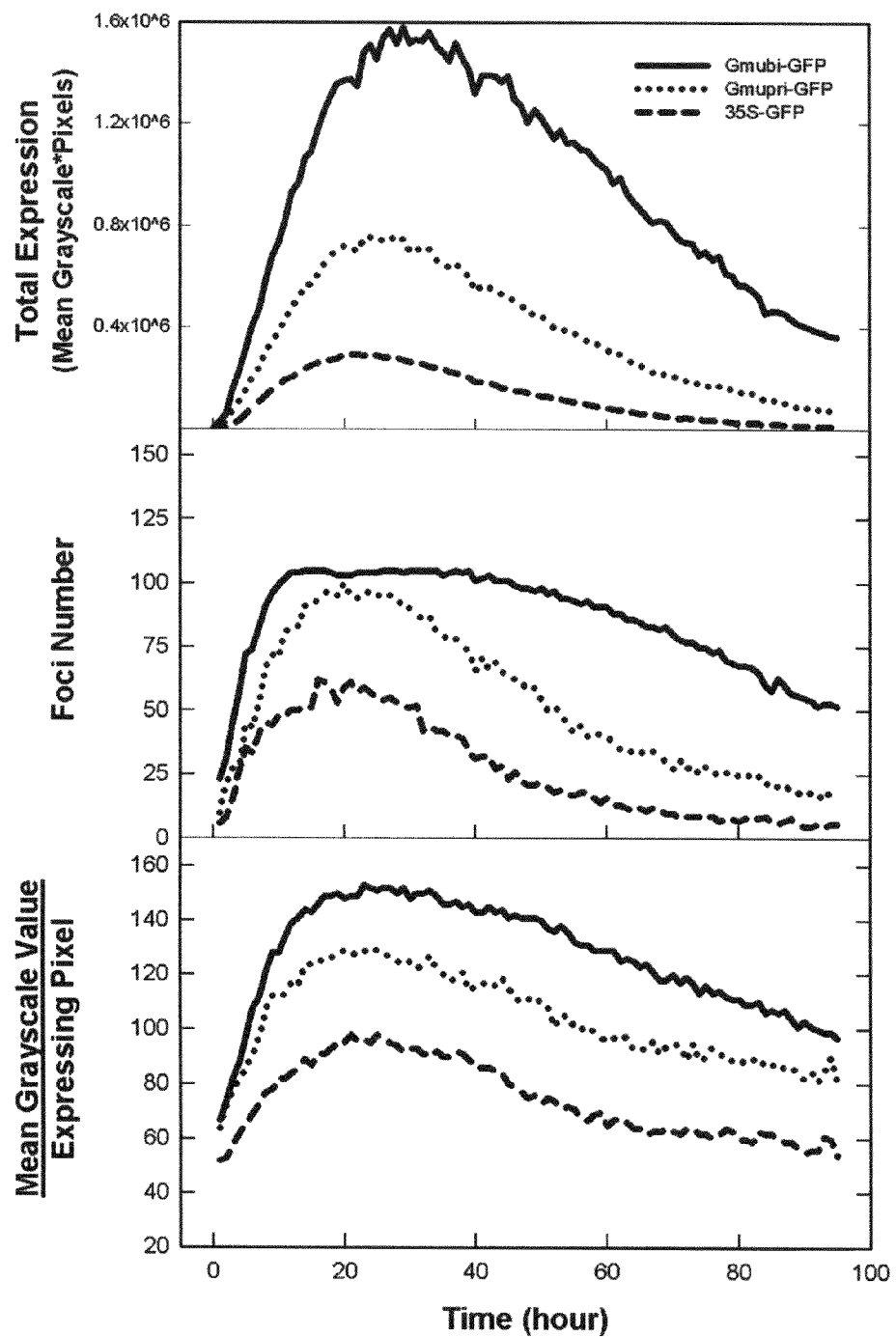

With semi-continuous tracking of GFP expression, it was possible to determine precisely the peak expression times for all of the different promoter constructs. The times for maximum expression of the CaMV35S, Gmubi and Gmupri promoters occurred at hours 22, 27 and 29, respectively (FIG. 3).

At those peak expression points, the Gmubi and the intronless Gmupri promoters had 5-fold ($1.58 \times 10^6 \pm 0.35 \times 10^6$; p=0.01) and over 2-fold ($0.76 \times 10^6 \pm 0.09 \times 10^6$; p=0.002) greater Total Expression compared to the CaMV35S ($0.30 \times 10^6 \pm 0.04 \times 10^6$) promoter. Gmubi and Gmupri promoters had an average of 105±21 (p=0.1) and 92±24 (p=0.3) foci expressing during their peak expression levels, respectively; whereas the CaMV35S promoter averaged 61±7 foci during its peak expression (FIG. 3).

Although Total Expression values for Gmubi continually increased to the peak expression at 27 hours (FIG. 3), the Focus Number for Gmubi reached a plateau at hour 15 and did not increase with increasing expression levels. An increase in expression paralleled the increase in focus number for all of the other constructs.

Analysis of GmHSP90L Promoters

Figure 4:
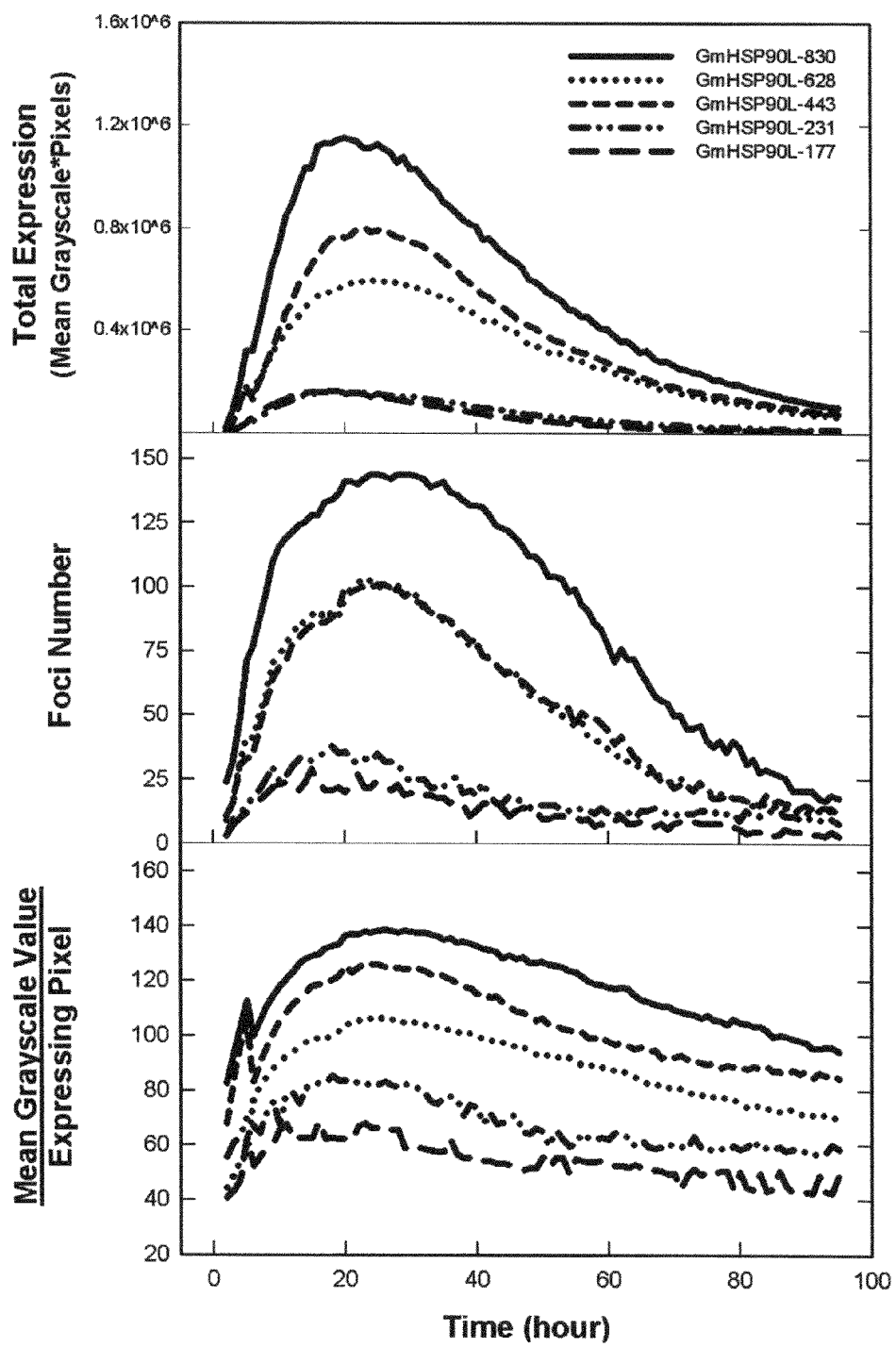

Analysis of the 5 different lengths of the GmHSP90L promoter showed that the largest promoter (GmHSP90L-830) displayed both the highest Total Expression value ($1.15 \times 10^6 \pm 0.27 \times 10^6$) and Focus Number (141±29; FIG. 4).

Truncation of the GmHSP90L promoter region to either 628 or 443 nucleotides resulted in roughly 50% reductions in both the Total Expression value and Focus Number. These two truncated promoters appeared to act similarly with regard to intensity and timing of GFP expression. A further reduction of the GmHSP90L promoter to either 231 or 177 nucleotides resulted in a further decline in Total Expression and the Focus Number (FIG. 4).

Discussion

Lima Bean Cotyledonary Transient Assay

Lima bean cotyledons, which were used as the target tissue in this example, have physiological and morphological characteristics that make them ideal for monitoring transient expression of GFP using the automated image collection system. The adaxial surface of the lima bean cotyledon is flat, which minimizes the variation in focal planes, allowing the collection of sharp, focused images. In addition, the tissue contains relatively large cells which yield distinct, GFP-expressing foci following successful DNA introduction. Lastly, this tissue contains minimal amounts of chlorophyll which may interfere with GFP fluorescence (Billinton and Knight 2001).

Evaluation of embryogenic cultures of soybeans (Finer 1988) and soybean seedling cotyledons (prepared similarly to the lima bean cotyledons) did not give consistent or useful results (data not shown). The small unresponsive areas in the lima bean cotyledons that were occasionally observed did not result from bombardment damage, as they were also observed (as light areas) in cotyledons that were never bombarded. These areas were avoided in image analysis and may represent parts of the cotyledon that were late to resume active metabolism following seed imbibition. Lima bean cotyledons provide the most robust and consistent transient GFP expression results of any system that we have evaluated. To our knowledge, this is the first report of the use of lima bean cotyledonary tissue for evaluating plant promoters or transient GFP expression.

Automated Image Capture

The ability to collect and analyze images from the same pieces of tissue over time adds another dimension to promoter characterization. This system allows tracking of GFP expression dynamics in single pieces of tissue, which is impossible with other reporter genes. Data was generated on both promoter strength and the timing of maximum GFP expression. As a recommendation for general observation of transient GFP expression, 24 hours post-introduction provided relatively consistent results with this target tissue.

In general, the promoters which generated high Focus Numbers also yielded the highest Total Expression values. Focus Number, or "spot count", has been the classical method for reporting successful DNA introduction via particle bombardment (Klein et al. 1987). As DNA introduction via particle bombardment is a physical process, the same number of cells should be penetrated by the particles for each bombardment. The Focus Numbers reported here suggest that there is a threshold for the detection of GFP expression. At the lower levels of GFP expression, a threshold appears to be required before a GFP focus can be visualized.

Using the detection methods described herein, many of the cells that were penetrated by particles carrying the CaMV35S-controlled gfp construct obviously did not express GFP at detectable levels. For the Gmubi and Gmupri comparisons, the same maximum numbers of cells were visualized using each promoter, with the increase in expression levels resulting from higher expression levels per cell.

Gmubi and Gmupri Promoters

Although ubiquitin promoters have been isolated and characterized from maize (Christensen et al. 1992), tobacco (Plesse et al. 2001), *Arabidopsis* (Callis et al. 1987), potato (Garbarino et al. 1995), tomato (Rollfinke et al. 1998) and rice (Wang and Oard 2003), this is the first report describing a ubiquitin promoter from soybean.

All of these ubiquitin promoters show similar characteristics, including the presence of a leading intron which can contribute to increased promoter strength. Removal of the intron from the rice promoter resulted in a complete loss of promoter activity (Wang and Oard 2003) while removal of the intron from the tobacco promoter resulted in a reduction in promoter strength and an alteration in tissue-specific expression (Plesse et al. 2001). The maize ubiquitin promoter with its intron has been used extensively over the years to obtain high levels of transgene expression in cereals (Callis et al. 1987; Fennell and Hauptman 1992; Christensen and Quail 1996).

In the present invention, expression of the gfp gene controlled by the intron-containing Gmubi promoter was much higher than with the pre-intronic Gmupri and the standard CaMV35S promoters (FIGS. 2, 3).

However, even without the intronic region, the Gmupri promoter was still substantially stronger than the CaMV35S promoter. Although many different forms of the CaMV35S promoter are available for plant transformation research, the version used here (Chiu et al. 1996) was the 423 nucleotide version and did not contain additional enhancer elements or regions of promoter duplication. Use of an even smaller CaMV35S promoter (−343 from the transcriptional start; Odell et al. 1985) did not give reduced transcript levels compared to the full-length promoter, showing that the 423 nucleotide CaMV35S promoter used in the present invention is comparable to the full-length promoter.

Given the high levels of GFP expression obtained with the Gmubi and Gmupri promoters used here, the addition of enhancer elements or duplication of promoter regions may lead to even higher levels of gene expression.

In addition to the ubiquitin intron, other introns from maize (act3, adh1-S, bz-1, sh1; Callis et al. 1987; Luehrsen and Walbot 1991; Vasil et al. 1989), rice (act1; McElroy et al. 1990) and oat (phyA3; Bruce and Quail 1990) have been used to enhance transgene expression in cereals. In dicot species, the effects of including an intronic region on promoter activity have been less definitive, resulting in no or minimal gene expression enhancements (Paszkowski et al. 1992; Plessse et al. 2001; Tanaka et al. 1990; Vancanneyt et al. 1990). Recently, however, a 5- to 6-fold enhancement of constitutive expression using a prolifin intron was reported in *Arabidopsis* (Jeong et al. 2006). Similarly, Chung et al. (2006) obtained a 2-fold increase in transient expression using the *Arabidopsis* EF 1α leading intron in Agroinfiltrated *Nicotiana benthalmiana* leaves. Internal truncations of this 5'UTR intron suggested that the absolute size of the intron along with at least 3 internal elements contributed to this 2-fold enhancement. Introns may enhance transgene expression through increased mRNA translational activity acquired from intron splicing and processing (Bourdon et al. 2001; Matsumoto et al. 1998).

A large enhancement of GFP expression was observed in the present invention when the intronic region from Gmubi was included in the promoter. The soybean intronic region may also contain one or more enhancer elements, as has been reported in the ubiquitin promoter regions of rice (Wang and Oard 2003), maize (Christensen and Quail 1996) and tobacco (Genschik et al. 1994).

GmHSP90L Promoters

Based on the Total Expression values and Focus Numbers, the GmHSP90L promoter constructs segregated into 3 distinct groups; the high expressing 830, the more moderately expressing 628 and 443 and the low expressing 231 and 177 (FIG. 4). It is believed by the inventor herein that the regions that were eliminated between the groups contained important regulatory regions that contributed to promoter activity. This promoter complexity was not unexpected, since regulation of plant Hsp90 genes can be intricate. For example, two maize Hsp90 genes exhibited distinct patterns of expression and heat shock induction in various tissues (Marrs et al. 1993), as did a pair of *Arabidopsis* cytosolic Hsp90 genes studied during embryo development (Prasinos et al. 2005).

The Total Expression value calculated for the GmHSP90L-830 construct (FIG. 4) was comparable to the value obtained with the Gmubi promoter (FIG. 3).

The largest soybean promoters, therefore, showed the highest activities in this example. The Gmupri and the GmHSP90L-628 and GmHSP90L-443 promoters presented similar expression profiles while the smallest GmHSP90L promoters 177 and 231 showed expression levels that were comparable to the CaMV35S promoter, which had the lowest activity of all the promoters. Although evaluation of these promoter constructs gave fairly consistent results, transient gene expression may be influenced by the nature of the target tissue and the means of DNA introduction. For example, exposure of plants to a variety of stresses, including wounding, caused changes in transcript levels for both Hsp90 in tobacco (Rizhsky et al. 2002) and for hsf genes that regulate all hsp genes in *Arabidopsis* (Miller and Mittler 2006). In addition, stress-induction of the Ubi.U4 gene has been reported in tobacco (Plesse et al. 2001). Particle bombardment may contribute to stress induction, resulting in an increase in gene expression. Bombardment of tissues, stably transformed with GmHSP90L-gfp and Gmubi-gfp, constructs with "blank" particles, may help to address questions of wound induction of these promoters.

Although peak GFP expression times were somewhat different for the various constructs, all of the GFP expression curves generated in this study showed very similar profiles (FIGS. 3, 4).

An initial rapid increase in expression was followed by a slow decline. Although the early fate of the introduced DNA may be of paramount importance for the recovery of transgenics, very little is known about the early events following DNA introduction. The decline in transient expression could result from degradation of unincorporated DNAs or silencing of either unincorporated or integrated DNAs through RNAi (Baulcombe 2004). The decline could also result from cell death, as the expressing cells have walls that have been compromised from particle introduction. Lastly, a small number of foci did not fade but suddenly stopped expressing between one time point to the next (one hour). Disappearing foci were easily visualized through generation of time-lapse animations of the assembled image series.

The combination of digital imaging and image analysis, along with the use of GFP for gene expression tracking constitutes a powerful tool to evaluate promoters and the dynamics of gene expression. The automated image analysis system permits the continual monitoring and rapid quantification of gene expression over time while bombardment of lima bean cotyledons provides a standard transient expression assay system with reduced variation for use in comparative expression studies.

Although a transient assay may not precisely reflect expression in stably-transformed tissues, this transient assay system quantitatively evaluates a large number of independent events.

Use of the automated system can quickly provide valuable information on the characteristics of different promoters and factors which can influence gene expression, prior to the generation of stably-transformed plants.

Example 2

Use of Novel Soybean Promoters to Regulate Gene Expression

Four different promoters from soybean have been identified and characterized which regulate or control expression of an introduced marker gene in soybean. One of these promoters (Gmubi) was partly cloned using PCR, based on known sequence information and similarities between a known maize promoter and soybean genomic sequence information. The remaining promoters were cloned based on microarray expression data and EST sequences. All of the promoters have been additionally modified by truncation and fusion with other promoter/regulatory regions to generate an array of promoters with different intensities and specificities of expression.

The Gmubi promoters shows much higher constitutive expression than the CaMV35S promoter, which is a promoter standard. Other promoters show root-specific expression and/or activity only in early-staged embryos.

These promoters are useful for regulating transgene expression. They are native soybean promoters. Some of the promoters yield high expression levels which is desired for some transgenes while others appear to drive expression in the roots, which are useful for expression of a gene for pathogen resistance where root tissue is targeted by the pathogen.

The promoters have been characterized using the green fluorescent protein using both transient expression and stable expression data.

Very few soybean promoters have been characterized with most of the emphasis placed on seed-specific promoters (Chen et al., 1986; β-conglycinin and Cho el al, 1995; lectin). But, with the wealth of information generated from genomics and microarrays (Thibaud-Nissen et al, 2003), isolation of additional promoters from soybean is now feasible.

However, characterization of the promoters in soybean has been a challenge. The present method now provides for the ability to evaluate promoters, based on intensity of expression of the green fluorescent protein and our automated image collection and analysis system (Finer et al, 2006). The inventors herein have now generated quantitative data on promoter strength, using a transient expression system as well as expression in stably transformed tissues. The method described herein provides for the capability to track and quantify gfp gene expression in plant tissues, over time.

Figure 12A:
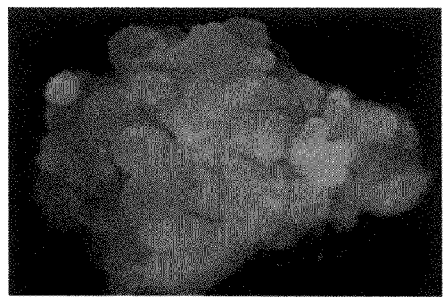
FIG. 12 are photographs showing proliferating D20 in embryonic tissue for: 35S, Gmupri, Actin, SHP90, Gmubi and non-transformed (Non-T).
Figure 12B:
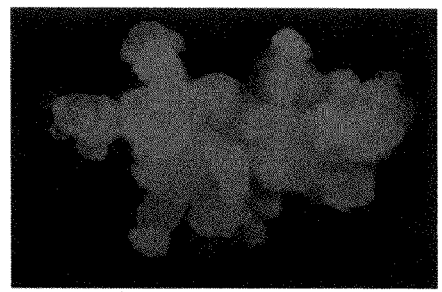
Figure 12C:
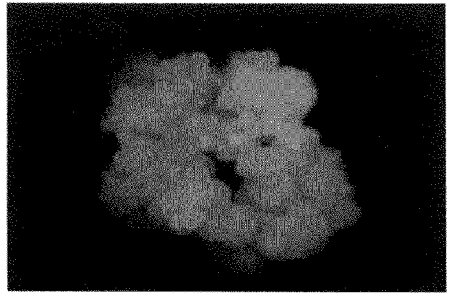
Figure 12D:
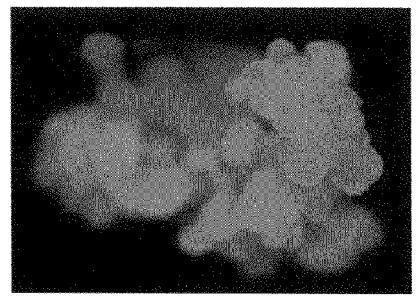
Figure 12:
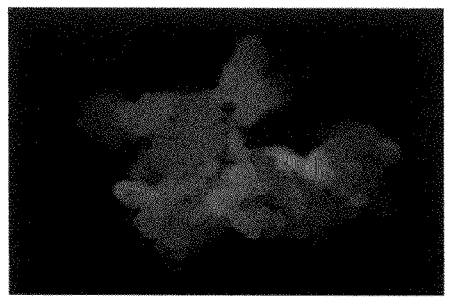
Figure 12F:

FIG. 12 shows photographs showing proliferating D20 in embryonic tissue for: 35S, Gmupri, Actin, SHP90, Gmubi and non-transformed (Non-T).

Figure 13:
FIG. 13 is a photograph showing HSP90 developing somatic embryos.

FIG. 13 is a photograph showing HSP90 developing somatic embryos.

Figure 14:
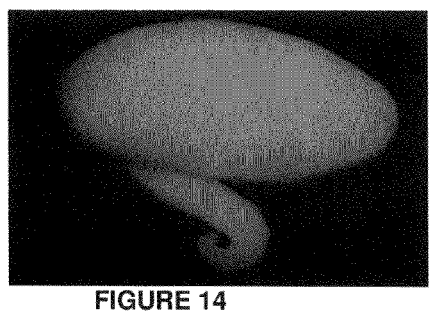
FIG. 14 is a photograph showing Gmubi in a germinating seedling.

FIG. 14 is a photograph showing Gmubi in a germinating seedling.

Figure 15A:
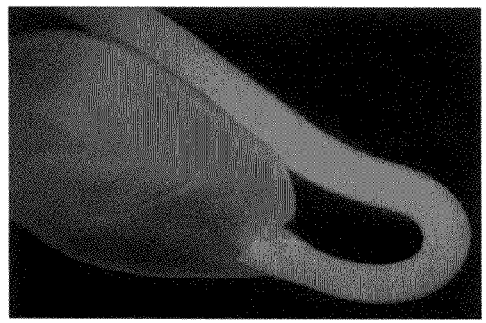
FIGS. 15A, 15B and 15C are photographs showing Gmubi in a germining seedling (FIG. 15A); in leaf veinal tissue (FIG. 15B); and in a petiole cross section (FIG. 15C).
Figure 15B:
Figure 15C:
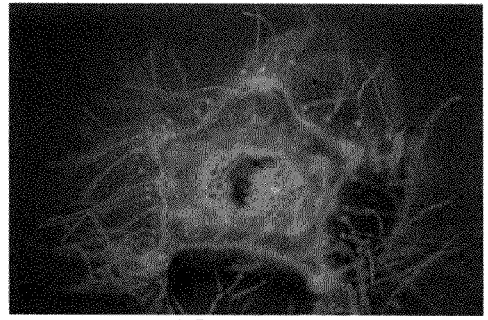
Figure 16A:
FIG. 16 is a series of photographs showing expression in roots: 35S, Actin, Gmubi, Gmupri, Extensin, and non-transformed (Non-T).
Figure 16B:
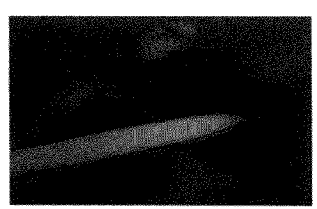
Figure 16C:
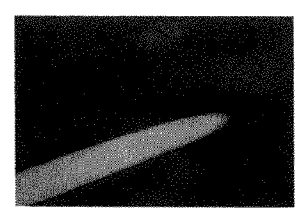
Figure 16D:
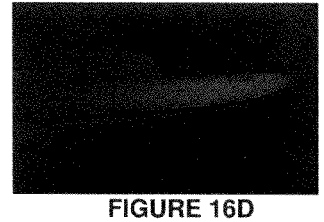
Figure 16E:
Figure 16F:
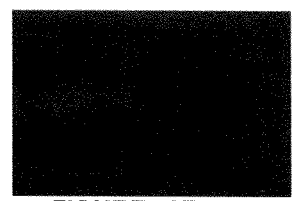

FIGS. 15A, 15B and 15C are photographs showing Gmubi in a germining seedling (FIG. 15A); in leaf veinal tissue (FIG. 15B); and in a petiole cross section (FIG. 15C).

FIG. 16 shows photographs showing expression in roots: 35S, Actin, Gmubi, Gmupri, Extensin, and non-transformed (Non-T).

The following is a description of the various promoters.

Figure 5A:
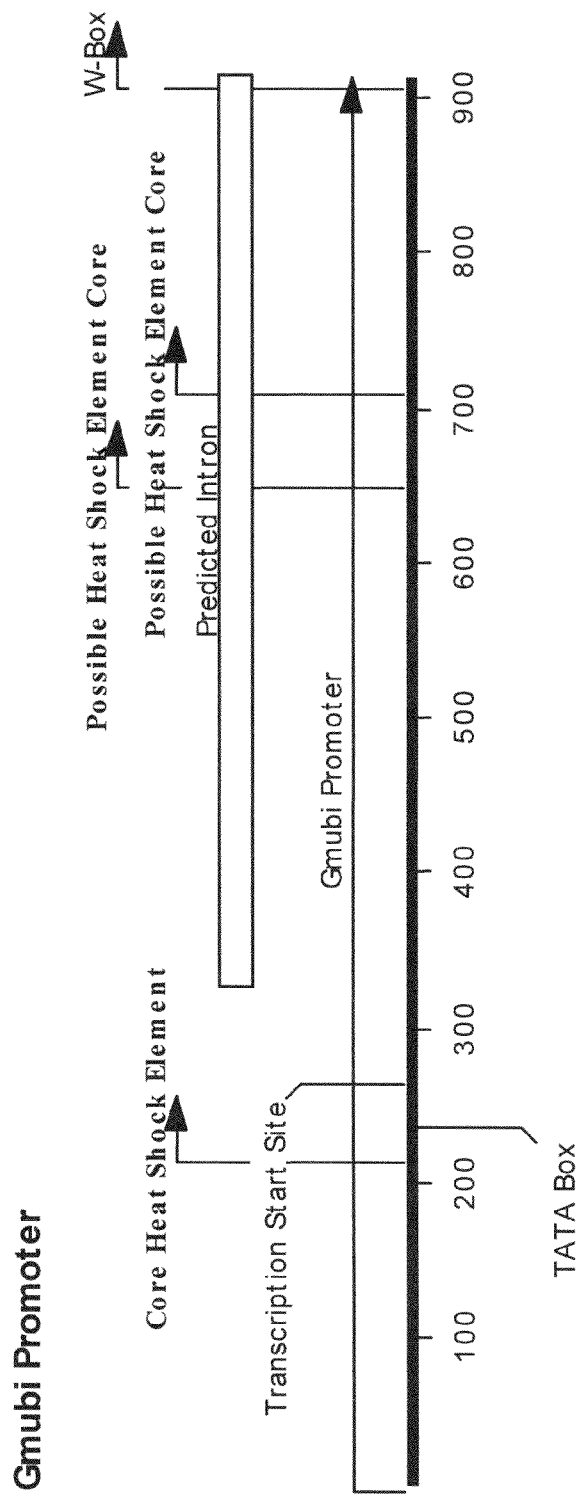

Gmubi Promoter is shown in FIG. 5B [SEQ ID NO: 1].

The information used in recovering the Gmubi (*Glycine max* ubiquitin) promoter was found in Genebank submission D28123: *Glycine max* SUBI-3 gene for ubiquitin.

This submission was made by Bao-Sen et al. in January, 1994, and contained 2170 by of genomic sequence information for a polyubiquitin gene.

It comprised 917 by of 5'UTR sequence, 919 by of coding sequence (containing four repeats encoding the ubiquitin monomer), and 332 by of 3'UTR sequence.

Analysis of the 5'UTR segment indicated it contained multiple motifs analogous to ones found in the maize polyubiquitin 1 promoter (Christiansen et al., 1992: Ling et al., 1995). These comprised a TATA box (−683 to −676) located just downstream of a consensus core heat shock regulatory element and just upstream of a consensus transcription start site, followed by putative intron (−592 to −1) which covered the entire remaining 5'UTR segment, with its consensus downstream splice junction precisely to the ATG start codon of the polyubiquitin ORF. (This intron contained two more possible heat shock core elements).

Figure 6A:
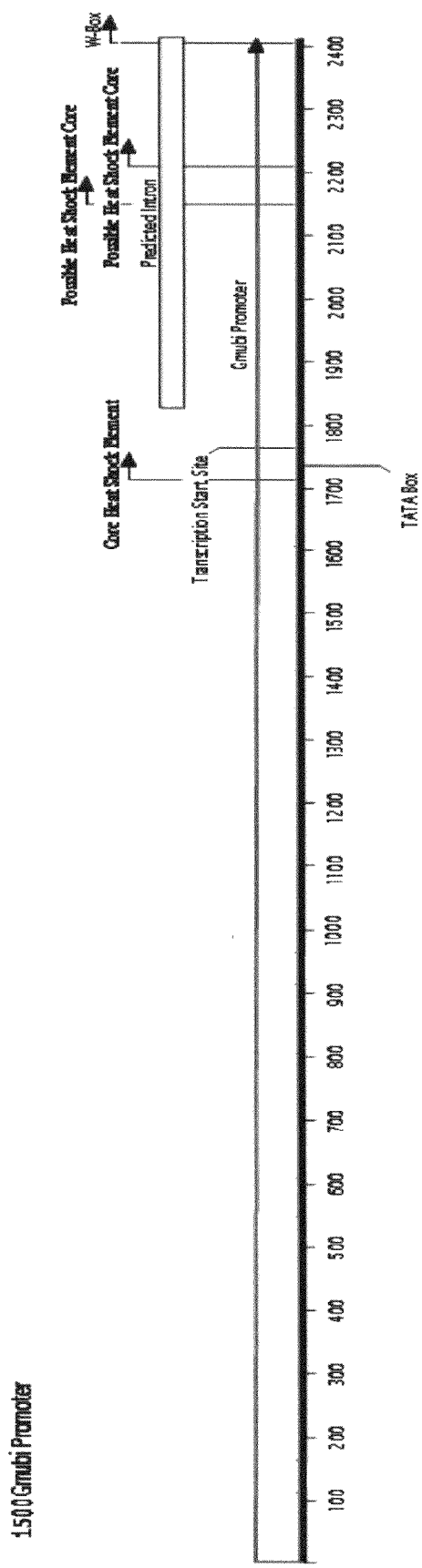

1500Gmubi is shown in FIG. 6B [SEQ ID NO: 2].

1500Gmubi is an extended version (~1500 bases) of Gmubi and shows 2-fold higher gene expression than Gmubi. Although Gmubi was cloned using PCR and some understanding of the similarities of the ubiquitin promoter sequences, the extension was added using the GenomeWalker™ system (Clonetech division, BD Biosciences). Of the Gmubi family of promoters, 1500 Gmubi shows the highest gene expression in this family.

Figure 7A:
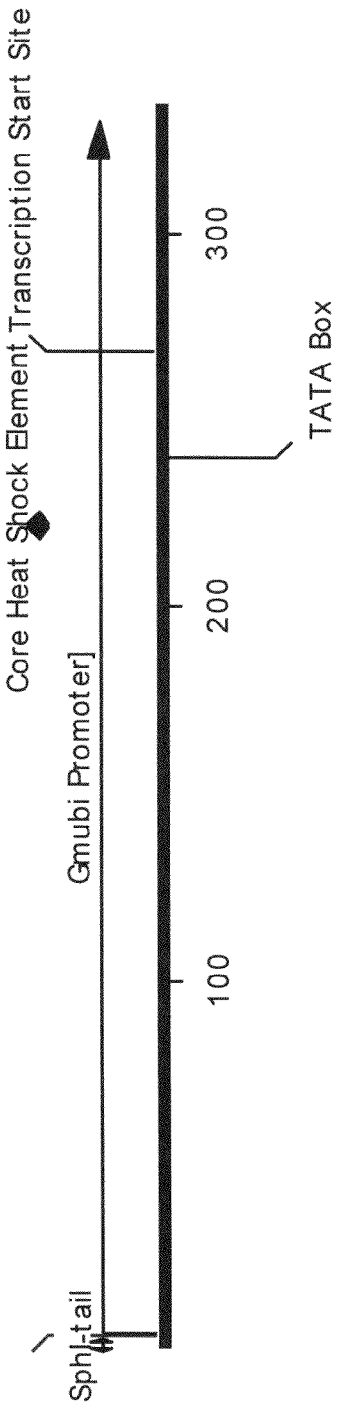

Gmupri (Gmubi pre-intronic) Promoter is shown in FIG. 7B [SEQ ID NO: 3].

The Gmupri (*G. max* ubiquitin pre-intron) promoter was recovered using a new reverse primer designed against the D28123 sequence to amplify only the 328 by segment of Gmubi preceding the intron (CGGATCCTTGAAGGGT-GCGGTAGGGAAAT [SEQ ID NO: 4], while adding 3' BamHI site. The SphI forward primer was used for the 5' end as before.

Figure 8A:
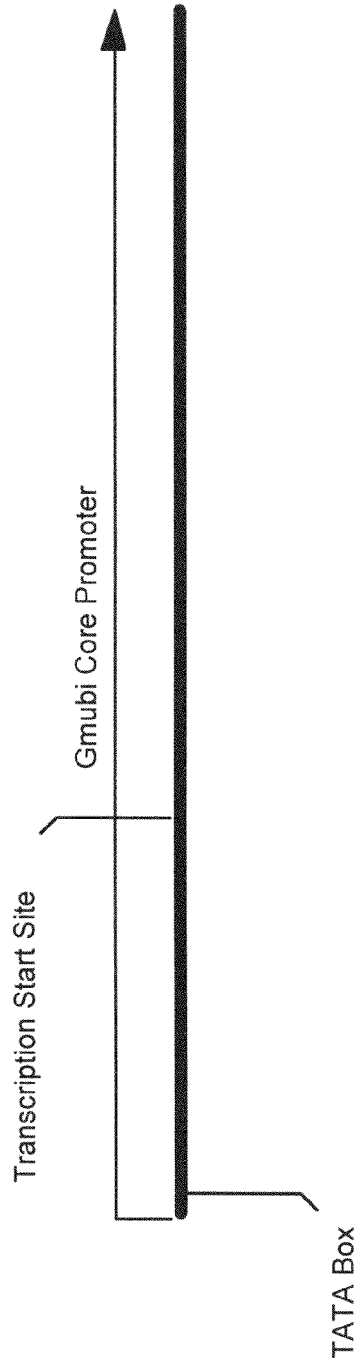

Gmucor (Minimal) Promoter is shown in FIG. 8B [SEQ ID NO: 5].

The Gmucor (Gmubi-core) promoter was recovered by designing a forward primer to amplify only the 93 by segment of Gmubi running from the TATA box and transcription start site to the start of the intron (CGTCGACTATAAAACGC-CCCTACACCC) [SEQ ID NO: 6], adding a 5' SalI site. The resulting core segment, which displays only weak promoter activity in isolation, was cloned into a destination vector containing an upstream MCS designed to accept 5' control segments from other promoters.

The *G. max* Actin (Gmactin), GmHSP90-like, and GmS11 promoters were recovered using the GenomeWalker™ system (Clonetech division, BD Biosciences). These three promoters were selected because transcripts for their corresponding ESTs are present at high levels in early embryogenic tissue from the surface of soybean cotyledons, with a steady decline in older tissue (Thibaud-Nissen et al, 2003). For recovery from the Genome Walker library, nested reverse primers, based upon each gene's corresponding EST, were constructed against the junction between the 5'UTR and the start of the ORF. The first-round reverse primer for each promoter was complementary to a segment just within the ORF of the corresponding EST. The secondary reverse primer was designed to be complementary to the 3' end of the upstream 5'UTR and the junction of the 5'UTR with the start codon of the EST, but with modifications of the sequences straddling the start codon to create an NcoI site encompassing the ATG of the EST ORF. Addition of the NcoI site allowed transcriptional fusion of recovered promoters directly to the GFP gene.

Figure 9A:
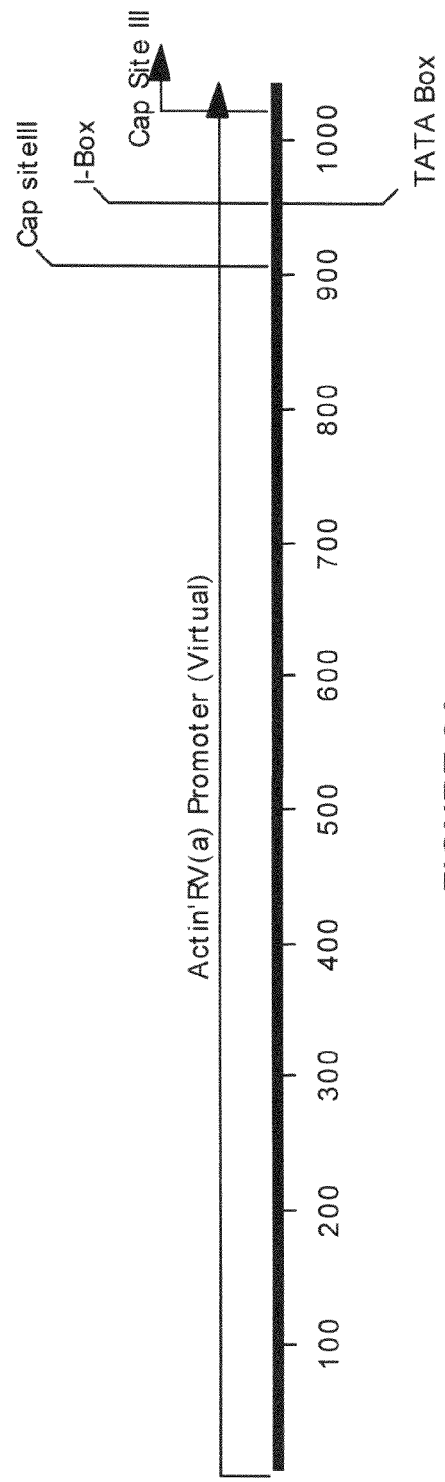

Gmactin Promoter FIG. 9 [SEQ ID NO: 7].

Reverse primers used to recover the Gmactin promoter were designed based on Genbank accession AW507553. The first-round primer was CAAACGAGGGGTTGAATATC-CTCGGCATC[SEQ ID NO: 8], while the secondary reverse primer was GCCATGGT-TGTTTAAGGTAAAAGATGTTTGTTTGT [SEQ ID NO: 9].

The last 111 bases of the 3' segment of a 1046 by NcoI fragment recovered from the EcoRV Genome Walker library matched the 111 base 5'UTR segment of EST AW507553, confirming that this fragment contained the genomic region 5' to the Gmactin coding region. This NcoI fragment comprises the Gmactin promoter.

Figure 10A:
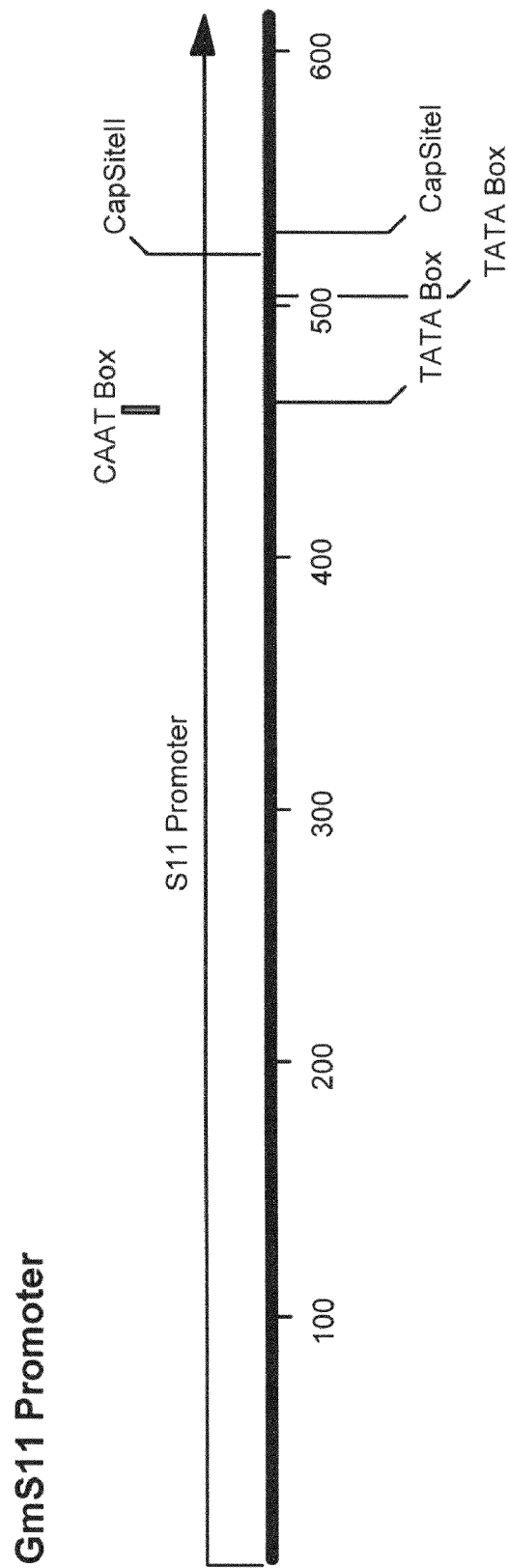

GmS11 Promoter is shown in FIG. 10 [SEQ ID NO: 10].

Reverse primers used to recover the GmS11 promoter were designed based on Genbank accession AW507568; first round GGTTGCTTCAGAAAAGCCTTCTCTGTTTGTTC [SEQ ID NO: 11] and second round GCCATGGTTGAG-GCACTGTTTCAAACG [SEQ ID NO: 12]. The final 65 by of the recovered isolate matched the 5' UTR of AW507568.

GmHSP90-like (GmHSP90L) Promoter and derivatives are shown in FIGS. 11B-F.

Reverse primers used to recover the GmHSP90L promoter were designed based on Genbank accession AW278784. The first round primer was TCAGCCTGGAAAG-CAAACGTCTCTGTCTC [SEQ ID NO: 13], and the second round primer was GCCATGGTCGATCTACGCGAGG-GAGAAC [SEQ ID NO: 14].

Two of the four GenomeWalker™ libraries yielded isolates with these primers, an 830 by isolate from the StuI library (the longest version of the promoter, HSP90L-830 (see FIG. 11B) [SEQ ID NO: 15], used in this example) and a 443 by isolate from the DraI library (HSP90L-443) [SEQ ID NO: 16]; the sequence of the latter was a perfect match for the last 443 by of the full-length HSP90L promoter. Each of these were cloned into our reporter vector using the 5' XmaI site located in the GenomeWalker™ linker and the engineered 3' NcoI site, creating a direct translational fusion to the start codon of the GFP gene. The last 31 bases of the 3' end both matched the 5'UTR segment of EST AW278784, confirming that each extended into the genomic region 5' to the GmHSP90L coding region.

Three additional versions of the HSP90L promoter were generated for analysis of the upstream control regions. Primers adding MluI tails (italics) were designed against regions 628 bp (CACGCGTTTGGAGATGACTGATTTATCT-TAGGAATG) [SEQ ID NO: 17], 231 by (CACGCGTAA-CAATTACGAGTGACGAGTC) [SEQ ID NO: 18], and 177 by (CACGCGTCGCTATATAACTAAGGGATCC) 5' [SEQ ID NO: 19] to the start codon, the last eliminating all control regions before the TATA box, including the adjacent putative SHP element. The corresponding HSP90-L promoter segments were amplified using each primer along with the second Walker primer, then cloned into our reporter vector using the new 5' MluI site and the 3' NcoI site added by the second Walker primer. The resulting versions of the promoter were designated HSP90L-628 [SEQ ID NO: 20], HSP90L-231 [SEQ ID NO: 21], and HSP90L-177 [SEQ ID NO: 22].

Figure 11A:
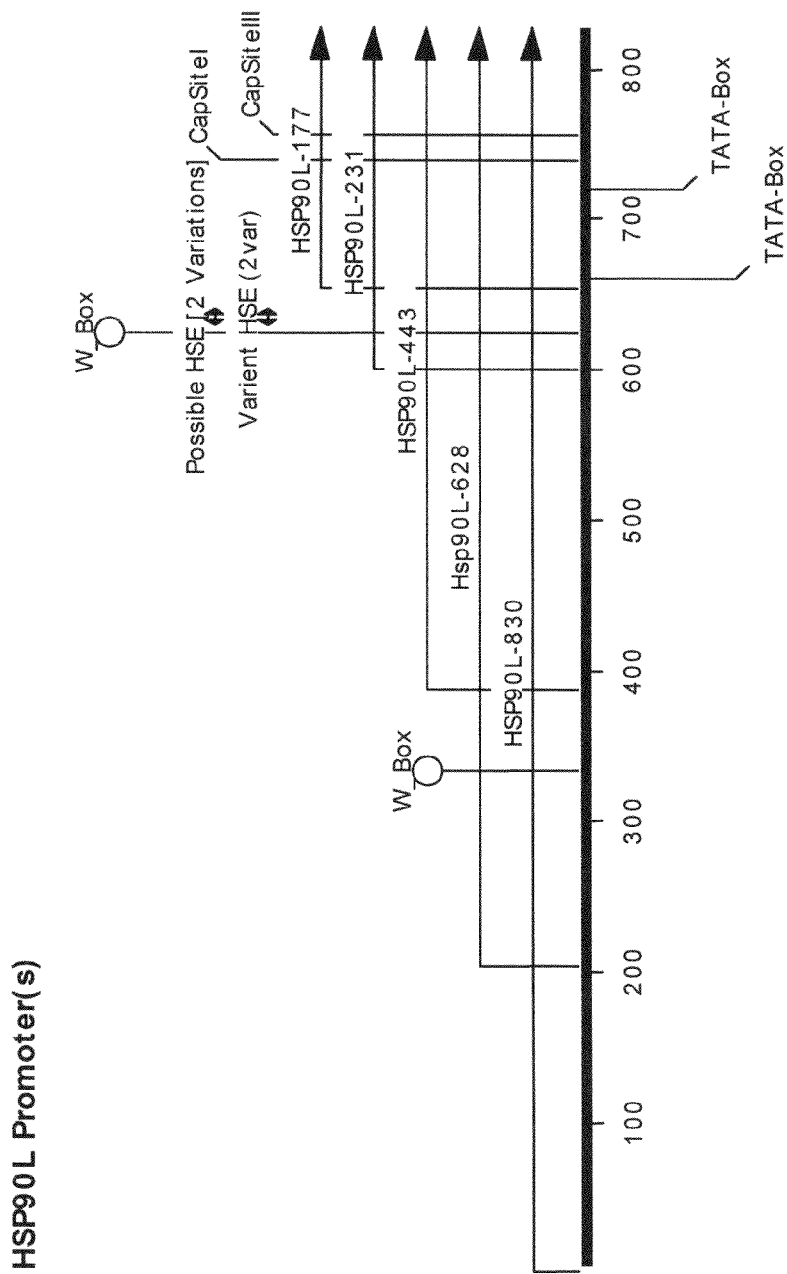

GmHSP90L-830 Promoter is shown in FIG. 11B [SEQ ID NO: 15].

GmHSP90L-628 Promoter is shown in FIG. 11C [SEQ ID NO: 20].

GmHSP90L-443 Promoter is shown in FIG. 11D [SEQ ID NO: 16].

GmHSP90L-231 Promoter is shown in FIG. 11E [SEQ ID NO: 21].

GmHSP90L-177 Promoter is shown in FIG. 11F [SEQ ID NO: 22].

Stable Transformation in Various Tissues

FIG. 17 contains a table that shows the soybean promoter GFP stable events for various promoters, listing the number of clones, the status of the clones and how transformation was confirmed.

FIG. 18 contains a table that shows, in soybean promoter GFP stable events, there was tissue-specific expression.

FIG. 19 contains photographs of the following clones: C7, C28, C30, C42, C57, and Jack, showing that Gmupri was express in pollen.

FIGS. 20A-20C are photographs showing GFP expression in a Gmupri C7 plant, specifically in the root tip, the lower stem, mid stem and leaf buds.

FIG. 21 is a photograph showing GFP expression in a Gmubi C72 seedling at 4 days.

FIG. 22 is a series of photographs showing GFP expression in a Gmubi C72 plantlet from bottom to top, i.e., from root through stem.

FIGS. 23A-23C are photographs showing GFP expression in a Gmubi C72 plantlet in the petiole (FIG. 23A), the leaf (FIG. 23B), and the shoot tip (FIG. 23C).

FIG. 24 is a photograph showing GFP expression in pollen in a Gmubi C72 clone.

FIGS. 25A-25D are photographs showing GFP expression in GmS11 clones: C-01 shown in FIGS. 25A, 25C and 25D; and C-12 shown in FIG. 25B.

FIGS. 26A and 26B are blots showing: in FIG. 26-Bgl II digest—no sited in either vector; and FIG. 26B showing Nhe I digest—single site in GFP vector.

FIGS. 27A-27D are photographs showing GFP expression in HSP90L seedlings for the following clones: HSP830-C60 (FIG. 27A); HSP830-C48 (FIG. 27B); HSP443-055 (FIG. 27C); and HSP830-C48 (FIG. 27D).

FIGS. 28A-28C are photographs showing HSP90L embryo induction for the following clones: HSP90L-C60-830 (FIG. 28A); HSP90L-057-4480 (FIG. 28B); and HSP90L-C30-830 (FIG. 28C).

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

REFERENCES

The citation of any reference herein is not an admission that such reference is available as prior art to the instant invention. Any publications mentioned in this specification are herein incorporated by reference. Any discussion of documents, acts, materials, devices, articles or the like which have been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Abebe T, Skadsen R, Patel M, Kaeppler H (2006) The Lem2 gene promoter of barley directs cell- and development-specific expression of gfp in transgenic plants. Plant Biotech J 4:35-44.

An G, Watson B D, Chiang C C (1986) Transformation of tobacco, tomato, potato and *Arabidopsis thaliana* using a binary Ti vector system. Plant Physiol 81:301-305.

Baulcombe D (2004) RNA Silencing in plants. Nature 431: 356-363.

Bendahmane A, Kanyuka K, Baulcombe D C (1999) The Rx gene from potato controls separate virus resistance and cell death responses. Plant Cell. 11:781-791.

Billinton N, Knight A W (2001) Seeing the wood through the trees: a review of techniques for distinguishing green fluorescent protein from endogenous autofluorescence. Anal Biochem 291:175-197.

Bourdon V, Harvey A, Lonsdale D M (2001) Introns and their positions affect the translational activity of mRNA in plant cells. EMBO Rep 2:394-398.

Bruce W B, Quail P H (1990) cis-Acting elements involved in photoregulation of an oat phytochrome promoter in rice. Plant Cell 2:1081-1089.

Buenrostro-Nava M T, Ling P P, Finer J J (2003) Development of an automated image collection system for generating time-lapse animations of plant tissue growth and green fluorescent protein gene expression. In: Vasil I (ed) Plant Biotechnology 2002 and Beyond, Kluwer Acad Pub, Dordrecht, pp 293-295.

Buenrostro-Nava M T, Ling P P, Finer J J (2005) Development of an automated image acquisition system for monitoring gene expression and tissue growth. Trans Amer Soc of Agric Engin 48:841-847.

Buenrostro-Nava M T, Ling P P, Finer J J (2006) Comparative analysis of 35S and Lectin promoters in transgenic soybean tissue using an automated image acquisition system and image analysis. Plant Cell Rep 25:920-926.

Callis J, Fromm M, Walbot V (1987) Introns increase gene expression in cultured maize cells. Gene Dev 1:1183-1200.

Chen Z L, Schuler M A, Beachy R N (1986) Functional analysis of regulatory elements in a plant embryo-specific gene. PNAS USA 83:8560-8564.

Cho M J, Widholm J M, Vodkin L O (1995) Cassettes for seed-specific expression tested in transformed embryogenic cultures of soybean. Plant Mol Biol Rep 13:255-269.

Christiansen A H, Sharrock R A, and Quail P H (1992). Maize polyubiquitin genes: structure, thermal perturbation of expression and transcript splicing, and promoter activity. Plant Mol. Biol. 18: 675-689.

Chiu W-L, Niwa Y, Zeng W, Hirano T, Kobayashi H, Sheen J (1996) Engineered GFP as a vital reporter in plants. Curr Biol 6:325-330.

Christensen A H, Quail P H (1996) Ubiquitin promoter based vectors for high level expression of selectable and/or screenable marker genes in monocotyledonous plants. Transgenic Res 5:213-218.

Christensen A H, Sharrock R A, Quail P H (1992) Maize polyubiquitin genes: structure, thermal perturbation of expression and transcript splicing, and promoter activity following transfer to protoplasts by electroporation. Plant Mol Biol 18:675-689.

Chung B Y W, Simons C, Firth A E, Brown C M, Hellens R P (2006) Effect of 5'UTR introns on gene expression in *Arabidopsis thaliana*. BMC Genomics 7:120.

Czarnecka E, Key J L, Gurley W B (1989) Regulatory domains of the Gmhsp17. 5-E heat shock promoter of soybean. Mol Cell Biol 9:3457-3463.

Fennell A, Hauptmann R (1992) Electroporation and PEG delivery of DNA into maize microspores. Plant Cell Rep 11:567-570.

Finer J J (1988) Apical proliferation of embryogenic tissue of soybean [*Glycine max* (L.) Merrill]. Plant Cell Rep 7:238-241.

Finer J J, Vain P, Jones M W, McMullen M D (1992) Development of the Particle Inflow Gun for DNA delivery to plant cells. Plant Cell Rep 11:232-238.

Finer J J, Beck S L, Buenrostro-Nava M T, Chi Y T, Ling PP (2006) In (Eds. S Dutta Gupta, Y Ibaraki) Plant Tissue Culture Engineering; Focus in Biotechnology, "Monitoring Gene Expression in Plant Tissues; Using green fluorescent protein with automated image collection and analysis" Springer, Dordrecht.

Finnegan J, McElroy D (1994) Transgene inactivation: plants fight back! BioTechnology 12:883-888.

Gamborg O L, Miller R A, Ojima K (1968) Nutrient requirements of suspension cultures of soybean root cells. Exp Cell Res 50:150-158.

Garbarino J E, Oosumi T, Belknap W R (1995) Isolation of a polyubiquitin promoter and its expression in transgenic potato plants. Plant Physiol 109:1371-1378.

Genschik P, Marbach J, Uze M, Feuerman M, Plesse B, Fleck J (1994) Structure and promoter activity of a stress and developmentally regulated polyubiquitin-encoding gene of *Nicotiana tabacum*. Gene 148:195-202.

Hartmann U, Valentine W J, Christie J M, Hays J, Jenkins G I, Weisshaar B (1998) Identification of UV/blue light-response elements in the *Arabidopsis thaliana* chalcone synthase promoter using a homologous protoplast transient expression system. Plant Mol Biol 36:741-754.

Jeong Y-M, Mun J-H, Lee I, Woo J C, Hong C B, Kim S-G (2006) Distinct roles of the first introns on the expression of *Arabidopsis* prolifin gene family members. Plant Physiol 140:196-209.

Kang T J, Kwon T H, Kim T G, Loc N H, Yang M S (2003) Comparing constitutive promoters using CAT activity in transgenic tobacco plants. Mol Cell 16:117-122.

Klein T M, Wolf E D, Wu R, Sanford J C (1987) High-velocity microprojectiles for delivering nucleic acids into living cells. Nature 327:70-73.

Ling L, Maillet D S, Frappier J R H, Walden D B, Atkinson B G (1995) Characterization, chromosomal mapping, and expression of different polyubiquitin genes in tissues from control and heat-shocked maize seedlings. Biochem Cell Biol 73:19-30.

Liu Z B, Ulmasov T, Shi X, Hagen G, Guilfoyle (1994) Soybean GH3 promoter contains multiple auxin-inducible elements. Plant Cell 6:645-657.

Luehrsen K R, Walbot V (1991) Intron enhancement of gene expression and the splicing efficiency of introns in maize cells. Mol Gen Genet 225:81-93.

Marrs K A, Casey E S, Capitant S A, Bouchard R A, Dietrich P S, Mettler L I, Sinibaldi R M (1993) Characterization of two maize HSP90 heat shock protein genes: expression during heat shock, embryogenesis, and pollen development. Dev Genet 14:27-41.

Matsumoto K, Montzka-Wasserman K, Wolffe A P (1998) Nuclear history of a pre-mRNA determines the translational activity of cytoplasmic mRNA. EMBO J 17:2107-2121.

McElroy D, Zhang W, Cao J, Wu R (1990) Isolation of an efficient actin promoter for use in rice transformation. Plant Cell 2:163-171.

Miller G, Mittler R (2006) Could heat shock transcription factors function as hydrogen peroxide sensors in plants? Ann Bot 98: 279-288.

Murashige T, Skoog F (1962) A revised medium for rapid growth and bioassays with tobacco tissue cultures. Physiol Plant 15:473-497.

Nagatani N, Takuni S, Tomiyama M, Shimada T, Tamiya E (1997) Semi-real time imaging of the expression of a maize polyubiquitin promoter-GFP gene in transgenic rice. Plant Sci 124:49-56.

Odell J T, Nagy F, Chua N H (1985) Identification of DNA sequences required for activity of the cauliflower mosaic virus 35S promoter. Nature 313:810-812.

Ow D W, Wood K V, Deluca M, de Wet J R, Helinski D R, Howell S H (1986) Transient and stable expression of the firefly luciferase gene in plant cells and transgenic plants. Science 234:856-859.

Paszkowski J, Peterhans A, Bilang R, Filipowicz W (1992) Expression in transgenic tobacco of the bacterial neomycin phosphotransferase gene modified by intron insertions of various sizes. Plant Mol Biol 19:825-836.

Piston D W, Patterson G H, Knobel S M (1999) Quantitative Imaging of the Green Fluorescent Protein (GFP). Method Cell Biol 58:31-48.

Plesse B, Criqui M-C, Dun A, Parmentier Y, Fleck J, Genschik P (2001) Effects of the polyubiquitin gene Ubi. U4 leader intron and first ubiquitin monomer on reporter gene expression in *Nicotiana tabacum*. Plant Mol Biol 45:655-667.

Ponappa T, Brzozowski A E, Finer J J (1999) Transient expression and stable transformation of soybean using the jellyfish green fluorescent protein. Plant Cell Rep 19:6-12.

Prasinos C, Krampis K, Samakovli D, Hatzopoulos P (2005) Tight regulation of expression of two *Arabidopsis* cytosolic Hsp90 genes during embryo development. J Exp Bot 56:633-644.

Rasband, W S, (1997-2006) ImageJ, U.S. National Institutes of Health, Bethesda, Md., USA. web cited rsb.info.nih.gov/i.

Richards H A, Halfhill M D, Millwood R J, Stewart C N (2003) Quantitative GFP fluorescence as an indicator of recombinant protein synthesis in transgenic plants. Plant Cell Rep 22:117-121.

Rizhsky L, Liang H, Mittler R (2002) The combined effect of drought stress and heat shock on gene expression in tobacco. Plant Physiol 130:1143-1151.

Rolfe S A, Tobin E M (1991) Deletion analysis of a phytochrome-regulated monocot rbcS promoter in a transient assay system. PNAS USA 88:2683-2686.

Rollfinke I K, Silber M V, Pfitzner U M (1998) Characterization and expression of a heptaubiquitin gene from tomato. Gene 211:267-276.

Sahoo P K, Soltani S, Wong A K C (1988) A survey of thresholding techniques. Comput Vision Graph 41:233-260.

Samac D A, Tesfaye M, Dornbusch M, Saruul P, Temple S J (2004) A comparison of constitutive promoters for expression of transgenes in alfalfa (*Medicago sativa*). Transgenic Res 13:349-361.

Santarém E R, Finer J J (1999) Transformation of soybean (*Glycine max* (L.) Merrill) using proliferative embryogenic tissue maintained on semi-solid medium. In Vitro Cell Dev Biol—Plant 35:451-455.

Stewart C N, Millwood R I, Halfhill M D, Ayalew M, Cardoza V, Kooshki M, Capelle G A, Kyle K R, Piaseki D, McCrum G, DiBenedetto J (2005) Laser-induced fluorescent imaging and spectroscopy of GFP transgenic plants. J Fluoresc 15:697-705.

Tanaka A, Mita S, Ohta S, Kyozuka J, Shimamoto K, Nakamura K (1990) Enhancement of foreign gene expression by a dicot intron in rice but not in tobacco is correlated with an increased level of mRNA and an efficient splicing of the intron. Nucleic Acids Res 18:6767-6770.

Thévenaz P, Ruttimann U E, Unser M (1998) A pyramid approach to subpixel registration based on intensity. IEEE Trans Image Process 7:27-41.

Thibaud-Nissen F, Shealy R T, Khanna A, Vodkin L O (2003) Clustering of microarray data reveals transcript patterns associated with somatic embryogenesis in soybean. Plant Physiol 132:118-136.

Vain P, Finer K R, Engler D E, Pratt R C, Finer J J (1996) Intron-mediated enhancement of gene expression in maize (*Zea mays* L.) and bluegrass (*Poa pratensis* L.). Plant Cell Rep 15:489-494.

Vancanneyt G, Schmidt R, O'Connor-Sanchez A, Willmitzer L, Rocha-Sosa M (1990) Construction of an intron-containing marker gene: splicing of the intron in transgenic plants and its use in monitoring early events in Agrobacterium-mediated plant transformation. Mol Gen Genet 220: 245-250.

Vasil V, Clancy M, Ferl R J, Vasil I K, Hannah L C (1989) Increased gene expression by the first intron of maize Shrunken-1 locus in grass species. Plant Physiol 91:1575-1579.

Vaucheret H (1994) Promoter-dependent trans-inactivation in transgenic tobacco plants; kinetic aspects of gene silencing and gene reactivation. C R Acad Sci 317:310-323.

Wang J, Oard J H (2003) Rice ubiquitin promoters: deletion analysis and potential usefulness in plant transformation systems. Plant Cell Rep 22:129-134.

What is claimed is:

1. A process for expressing nucleic acids in transgenic plants under the control of a soybean ubiquitin promoter, wherein the process comprises the following steps: linking a nucleic acid to be expressed to a promoter containing at least the Gmubi Promoter of SEQ ID NO:1 to form a construct; introducing into a plant the construct under conditions which enable the construct to be stably integrated into the genome of said plant; and expressing the nucleic acid under the control of the soybean Gmubi promoter of SEQ ID NO:1.

2. The process of claim 1, wherein the nucleic acid to be expressed is functionally linked to one or more further regulatory sequences.

3. The process of claim 1, wherein the nucleic acid encodes a protein selected from the group consisting of a selection marker, a reporter gene, an enzyme, a protein which mediates resistance to insects, viruses, bacteria, fungi or nematodes, a protein which mediates in plants resistance to drought, cold, heat or salt, an inhibitor, a lectin, an RNAase, a ribozyme, an antibody, a vaccine, a pharmaceutical, an anti-freezing protein, a cytochrome P-450 protein, a transcription activator or repressor and a protein involved in biosynthesis of fine chemicals.

4. The process of claim 1, wherein the construct contains one or more further polynuceotides under the control of the soybean ubiquitin promoter or of another promoter.

5. The process of claim 1, wherein the nucleic acid is expressed in the sense or antisense direction or in the sense and antisense directions.

6. The process of claim 1, wherein the nucleic acid construct is inserted between two T-DNA sections.

7. The process of claim 1, wherein the transgenic plant is a monocotyledonous or dicotyledonous plant.

8. The process of claim 1, wherein the transgenic plant is a monocotyledonous plant selected the group from consisting of corn, rice, triticale, wheat, barley, oats, rye grass, grass, coconut, palm and millet.

9. The process of claim 1, wherein the transgenic plant is a dicotyledonous plant selected from the group consisting of alfalfa, almond, Arabidopsis, avocado, bay, borage, calendula, canola, carrot, castor-oil plant, cocoa, coffee, cotton, eggplant, evening primrose, hazelnut, hemp, linseed, macadamia, manioc, mustard, oilseed olive, pea, peanut, pepper, pistachios, poplar, poppy, potato, pumpkin, punica, rape, safflower, sesame, soybean, sugar beet, sunflower, tagetes, tea, thistle, tobacco, tomato, verbascum, walnut, and wild roses.

10. The process of claim 1, wherein products produced in the transgenic plants due to expression of the nucleic acid are isolated after culturing of the plant.

* * * * *